US012746271B2

(12) United States Patent
Kim et al.

(10) Patent No.: US 12,746,271 B2
(45) Date of Patent: Sep. 29, 2026

(54) FAS-ASSOCIATED FACTOR 1 (FAF1)-LOADED EXOSOMES AND USE THEREOF AS ANTI-CANCER AGENT

(71) Applicant: KAINOS MEDICINE, INC., Seongnam-si (KR)

(72) Inventors: Eunhee Kim, Seoul (KR); Jeong-Hoon Han, Seongnam-si (KR)

(73) Assignee: KAINOS MEDICINE, INC., Seongnam-si (KR)

( * ) Notice: Subject to any disclaimer, the term of this patent is extended or adjusted under 35 U.S.C. 154(b) by 466 days.

(21) Appl. No.: 18/283,108

(22) PCT Filed: Mar. 30, 2022

(86) PCT No.: PCT/KR2022/004475
§ 371 (c)(1),
(2) Date: Sep. 20, 2023

(87) PCT Pub. No.: WO2022/211473
PCT Pub. Date: Oct. 6, 2022

(65) Prior Publication Data
US 2024/0156905 A1 May 16, 2024

(30) Foreign Application Priority Data
Mar. 30, 2021 (KR) ........................ 10-2021-0040990

(51) Int. Cl.
*A61K 38/17* (2006.01)
*A61K 9/127* (2025.01)
*A61P 35/00* (2006.01)
*C12N 5/071* (2010.01)
*C12N 5/09* (2010.01)
*G01N 33/50* (2006.01)

(52) U.S. Cl.
CPC .......... *A61K 38/1761* (2013.01); *A61K 9/127* (2013.01); *A61P 35/00* (2018.01); *C12N 5/0686* (2013.01); *C12N 5/0693* (2013.01); *G01N 33/5011* (2013.01); *C12N 2510/00* (2013.01)

(58) Field of Classification Search
None
See application file for complete search history.

(56) References Cited

U.S. PATENT DOCUMENTS

| | | | | |
|---|---|---|---|---|
| 11,319,360 | B2 | 5/2022 | Koh et al. | |
| 2005/0261190 | A1* | 11/2005 | Lee | C07K 14/47 514/19.3 |
| 2022/0214361 | A1 | 7/2022 | Kim | |
| 2022/0317132 | A1 | 10/2022 | Baek et al. | |

FOREIGN PATENT DOCUMENTS

| | | | | |
|---|---|---|---|---|
| CN | 101899443 | A * | 12/2010 | |
| KR | 10-2004-0101707 | A | 12/2004 | |
| KR | 102049199 | B1 * | 11/2019 | G01N 33/6896 |
| KR | 10-2053065 | B1 | 12/2019 | |
| KR | 10-2129067 | B1 | 7/2020 | |
| KR | 10-2021-0031137 | A | 3/2021 | |
| WO | 96/40864 | A1 | 12/1996 | |
| WO | WO-2021193802 | A1 * | 9/2021 | G01N 33/57484 |

OTHER PUBLICATIONS

NCBI accession No. NP_008982 (printed 2026).*
Carvalho et al (Frontiers in Bioscience, Landmark, Jan. 1, 2020; 25:398-436).*
Hurwitz et al (Oncotarget, 2016, 7(No. 52):86999-87015).*
KR102049199, Kim, published Nov. 26, 2019 with English translation of description.*
KR102049199, Kim, published Nov. 26, 2019 with English translation of claims.*
CN101899443, Jin et al, published 2010 with English translation of description.*
CN101899443, Jin et al, published 2010 with English translation of claims.*
Johnsen et al (Biochimica et Biophysica Acta, 2014, 1846:75-87).*
English Translation of description of WO 2021/193802, Ueno et al., filed Mar. 25, 2021, claiming priority to Mar. 26, 2020.*
"FAS-associated factor 1 [*Homo sapiens*]", NCBI, Genbank 2021, Reference Sequence: NP_008982.1, Feb. 16, 2021, pp. 1-8 (8 pages total).
Genbank, fas-associated factor 1 [*Homo sapiens*], GenBank: AAD51886.1, https://www.ncbi.nlm.nih.gov/protein/AAD51886.1, Aug. 31, 1999, 2 pages.
Gyeongrin Park, et al., "A novel function of FAF1, which induces dopaminergic neuronal death through cell-to-cell transmission", Cell Communication and Signaling, 2020, pp. 1-17, vol. 18, thesis No. 133.
Genbank, FAS-associated factor 1 [*Homo sapiens*], NCBI Reference Sequence: NP_008982.1, Nov. 19, 2020, 3 pages.
Korean Patent Office, Notice of Third Party Submission in Korean Patent Application No. 10-2022-0039307 issued on Nov. 28, 2022.
International Search Report for PCT/KR2022/004475 dated Jun. 30, 2022 (PCT/ISA/210).

(Continued)

*Primary Examiner* — Laura B Goddard
(74) *Attorney, Agent, or Firm* — Sughrue Mion, PLLC

(57) ABSTRACT

Fas-associated factor 1 (FAF1) protein-loaded exosomes and a cancer treatment using FAF1 protein-loaded exosomes are disclosed. FAF1 protein-loaded exosomes are isolated from HEK 293 cells in which FAF1 having a known tumor-suppressive function is overexpressed and administered the FAF1 protein-loaded exosomes to various tumor models in which pancreatic cancer cells (MIA PaCa-2), lung cancer cells (A549), colon cancer cells (HCT 116), liver cancer cells (Hep3B), breast cancer cells (MDA-MB-231), kidney cancer cells (Caki-1) and cervical cancer cell (HeLa cell) are transplanted into nude mice through intratumoral injection. The administration exhibited tumor growth inhibitory effects remarkably greater than those of a control group not treated with FAF1.

8 Claims, 24 Drawing Sheets

Specification includes a Sequence Listing.

(56) References Cited

OTHER PUBLICATIONS

Xiaoyin Zhao et al., "Exosomes as drug carriers for cancer therapy and challenges regarding exosome uptake", Biomedicine & Pharmacotherapy, 2020, vol. 128 No. 110237, pp. 1-9 (9 pages).
Léa Tourneur et al., "Absence or Low Expression of Fas-Associated Protein with Death Domain in Acute Myeloid Leukemia Cells Predicts Resistance to Chemotherapy and Poor Outcome", Cancer Research, Nov. 1, 2004, vol. 64, pp. 8101-8108 (8 pages).
Jeong-Hoon Han et al., "Abstract 1728: Exosomal delivery of Fas-associated factor 1 (FAF1), a multifunctional tumor suppressor and genuine exosome cargo, effectively antagonizes tumor growth", Cancer Res, 2023, vol. 83 (7_Supplement), 2 pages.
Extended European Search Report dated Mar. 11, 2025, issued in European Application No. 22781592.5.
Araujo-Abad, et al., "Exosomes: from basic research to clinical diagnostic and therapeutic applications in cancer", Cellular Oncology, 2024, pp. 1-25 (25 pages).
Choi, et al., "Targeted Delivery of Exosomes Armed with Anti-Cancer Therapeutics", Membranes, 2022, vol. 12, No. 85, pp. 1-17 (17 pages).

* cited by examiner

【Fig. 1】
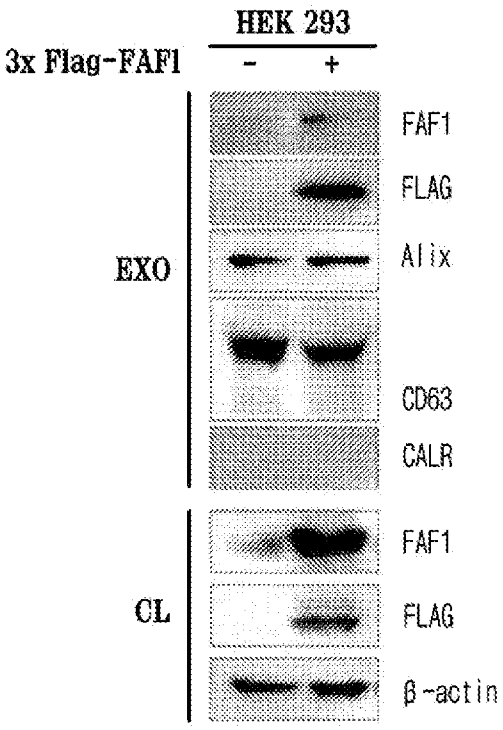
【Fig. 2】
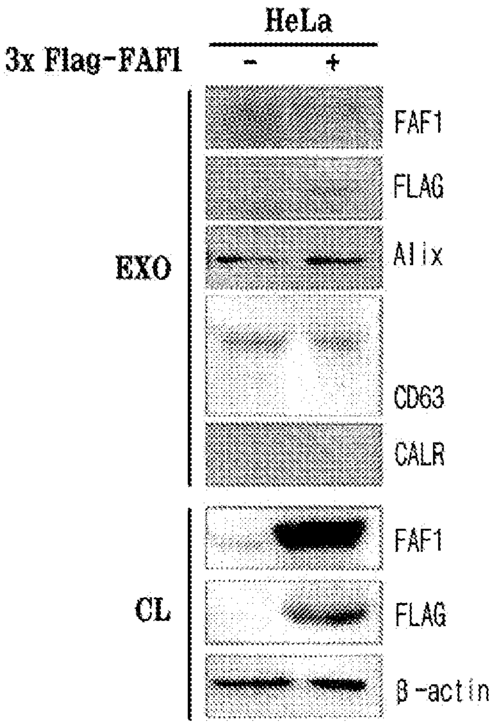

【Fig. 3】
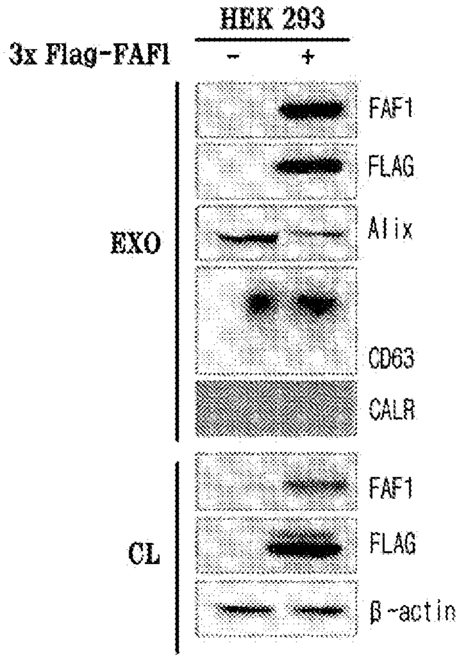
【Fig. 4】
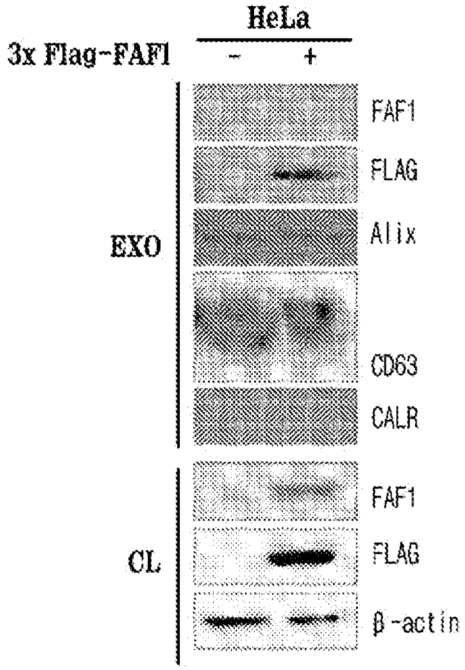

【Fig. 5a】
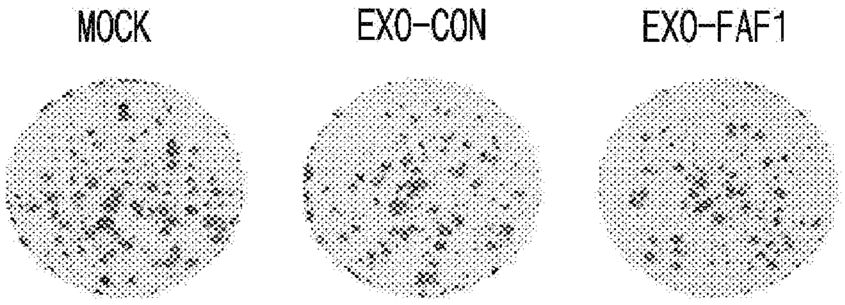
【Fig. 5b】
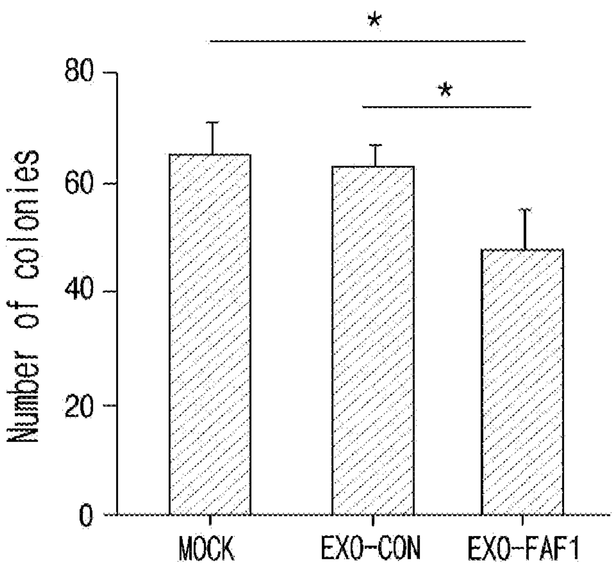
【Fig. 6a】
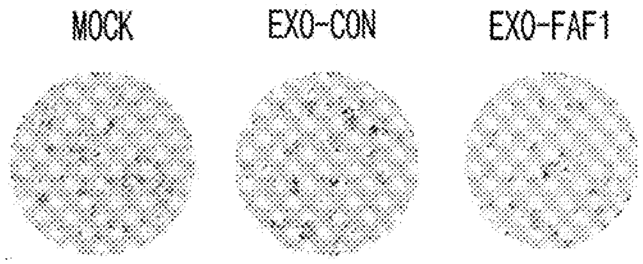

【Fig. 6b】
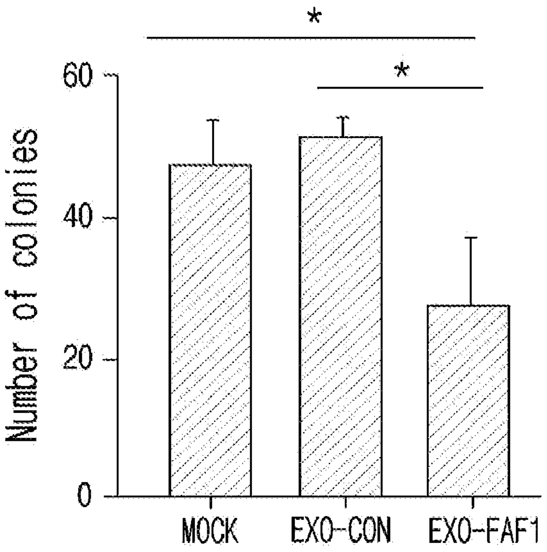
【Fig. 7a】
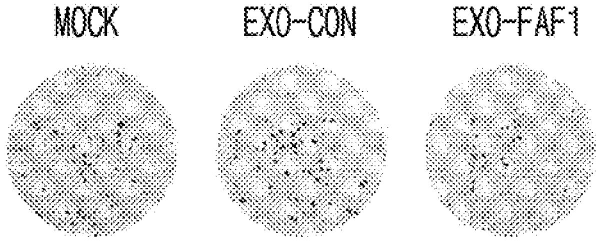
【Fig. 7b】
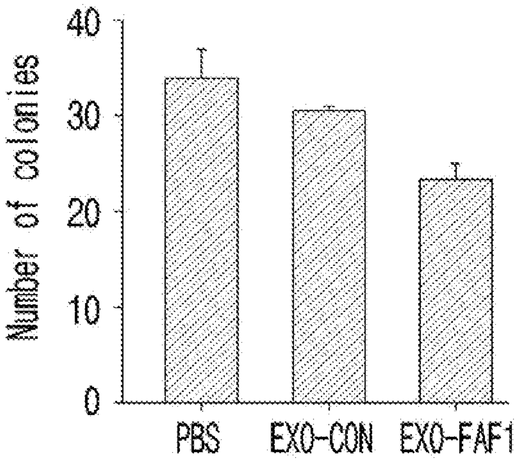

【Fig. 8a】
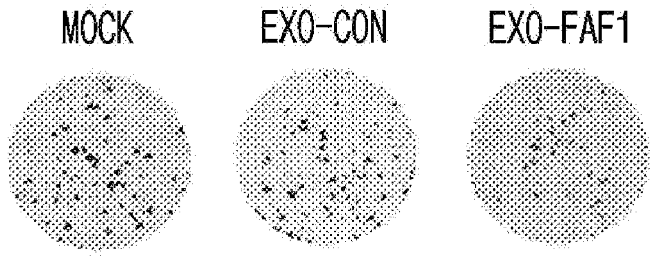
【Fig. 8b】
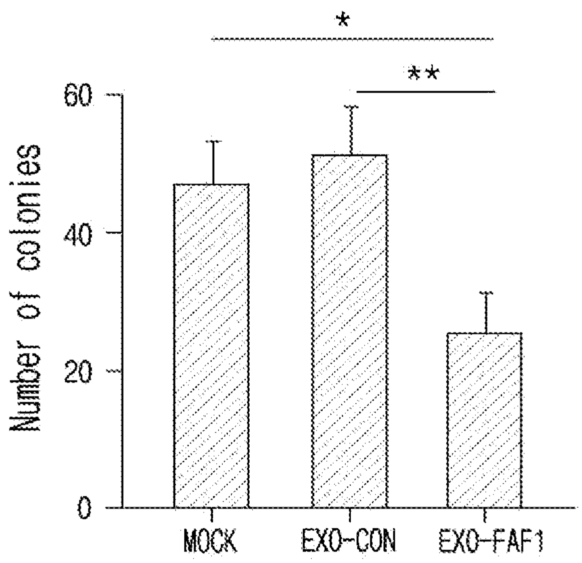
【Fig. 9a】
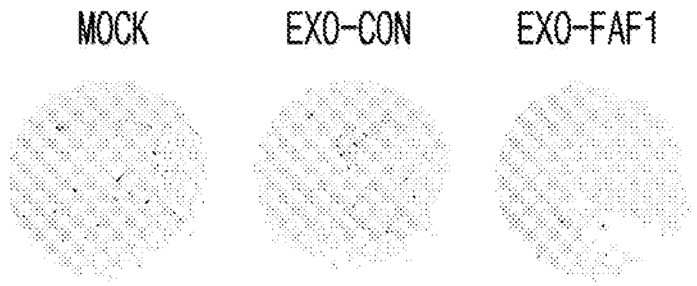

【Fig. 9b】
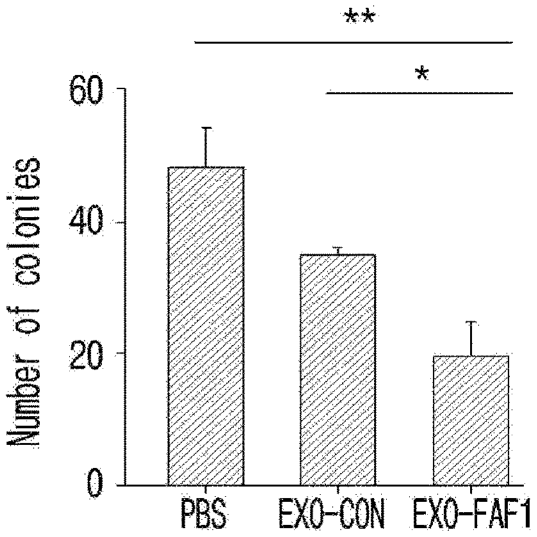
【Fig. 10a】
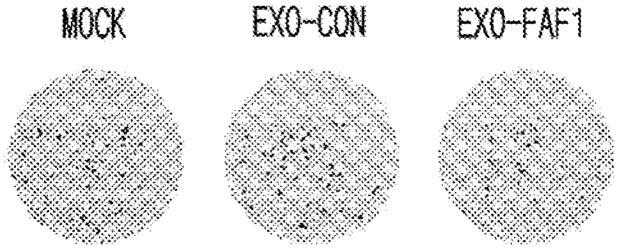
【Fig. 10b】
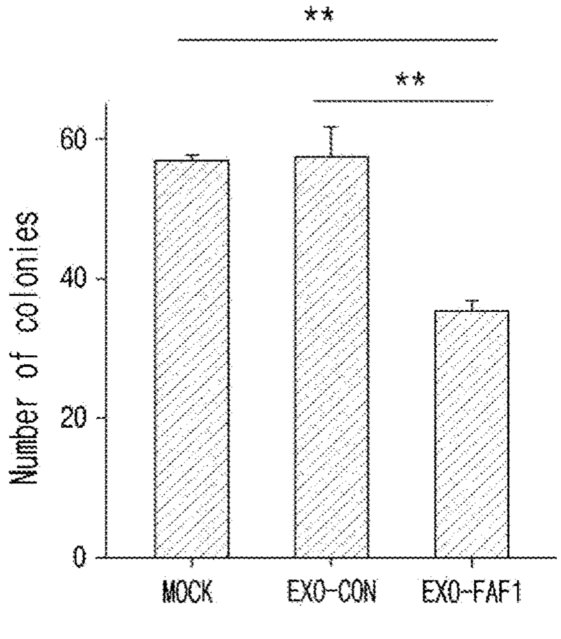

【Fig. 11a】
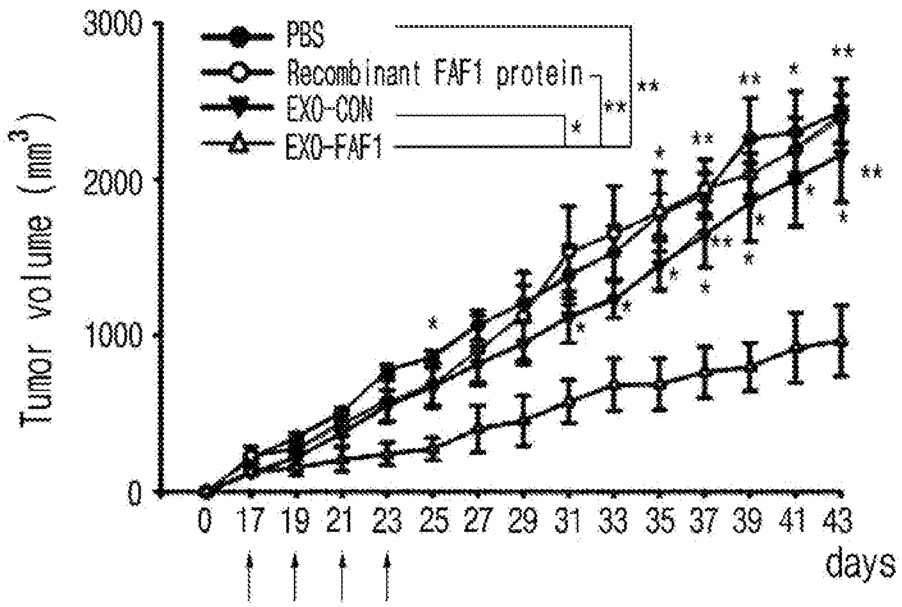
【Fig. 11b】
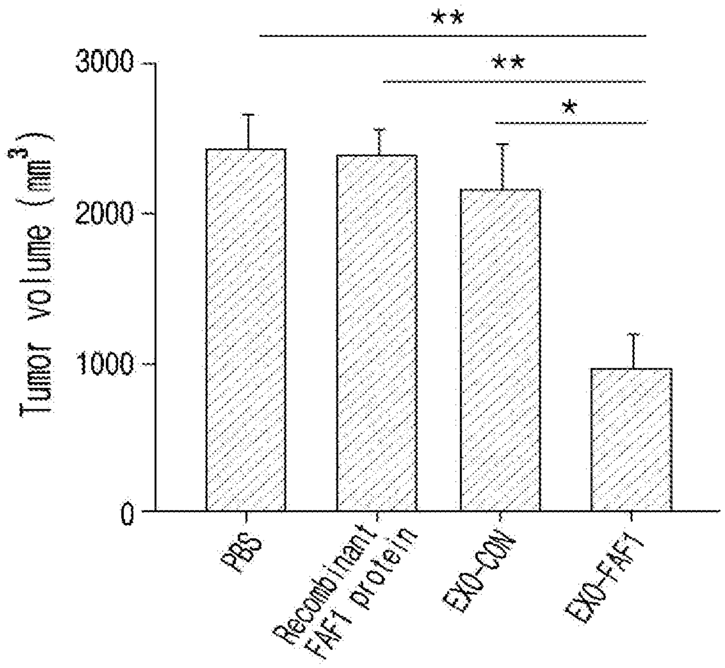

【Fig. 11c】
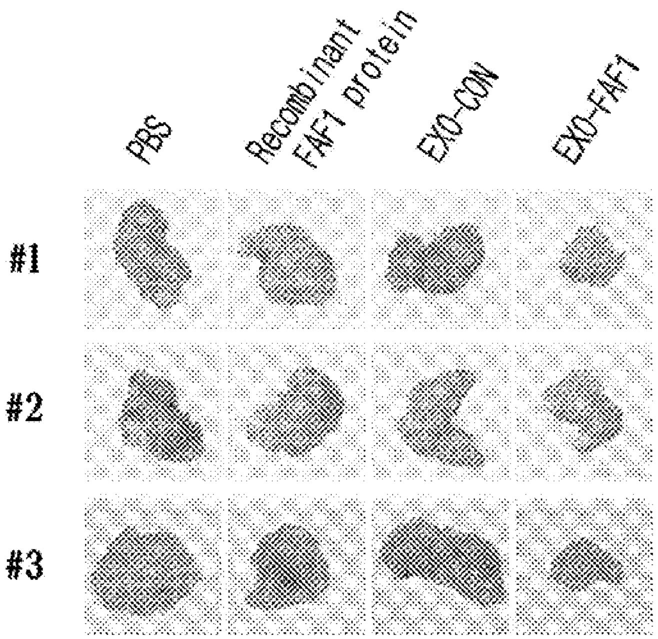
【Fig. 11d】
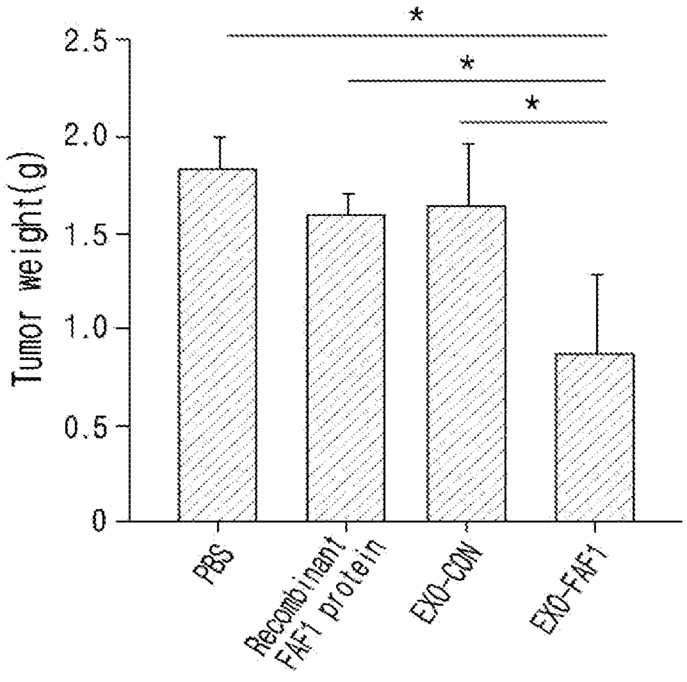

【Fig. 11e】
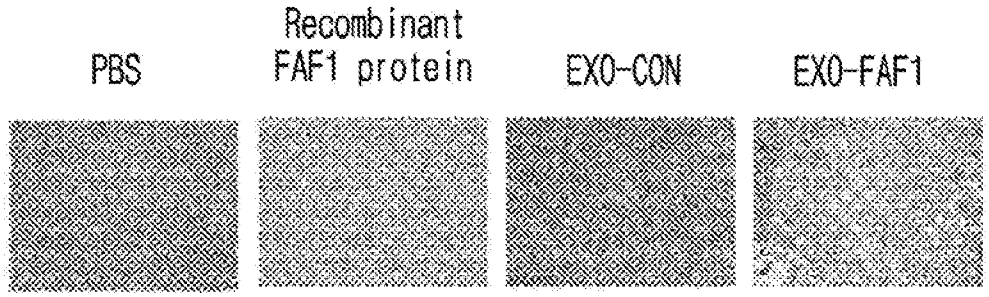
【Fig. 12a】
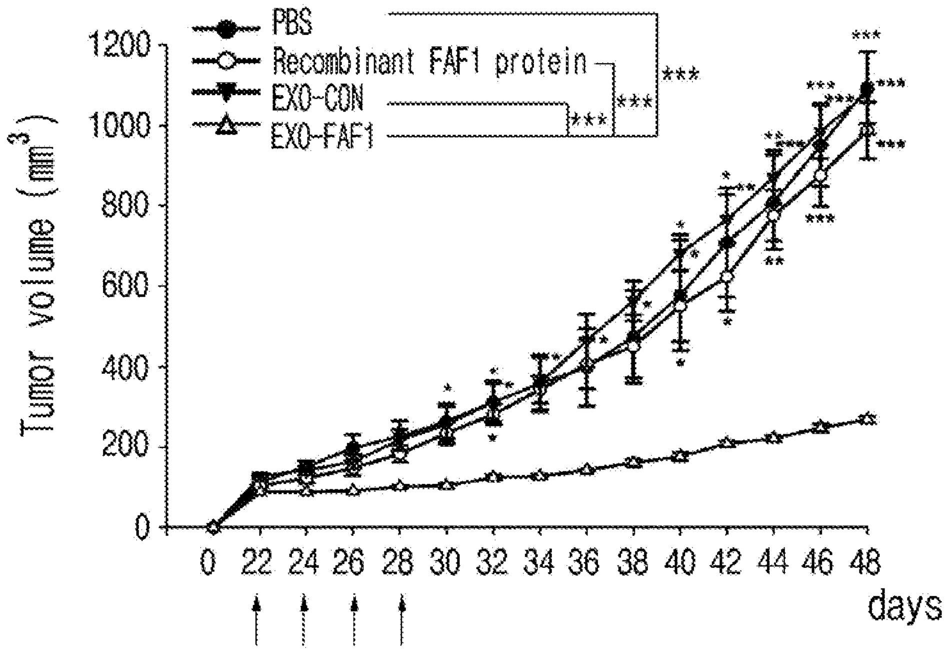

【Fig. 12b】
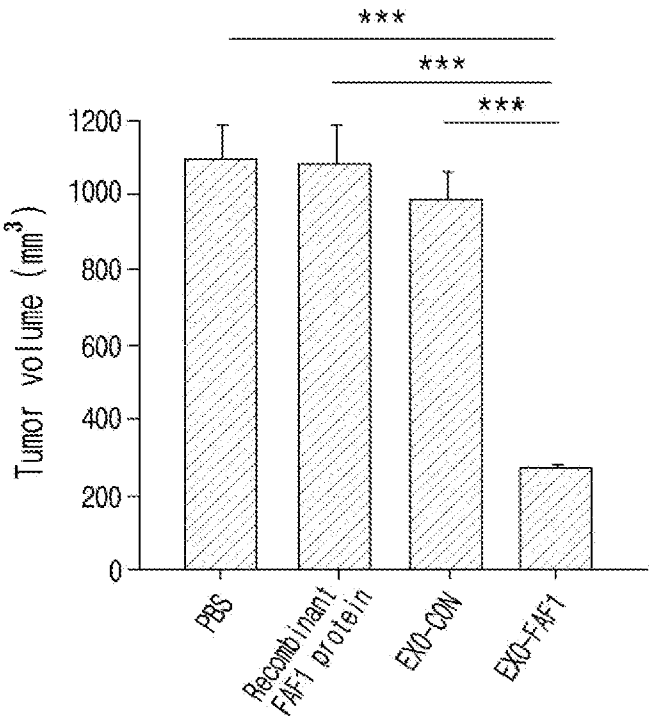
【Fig. 12c】
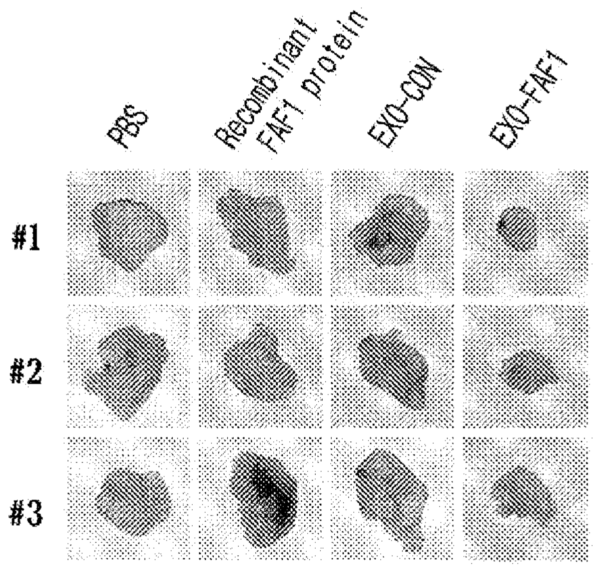

【Fig. 12d】
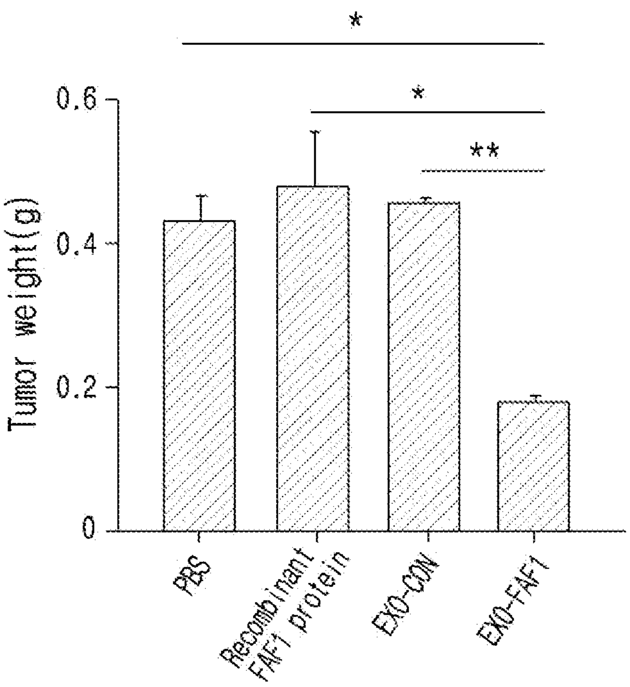
【Fig. 12e】
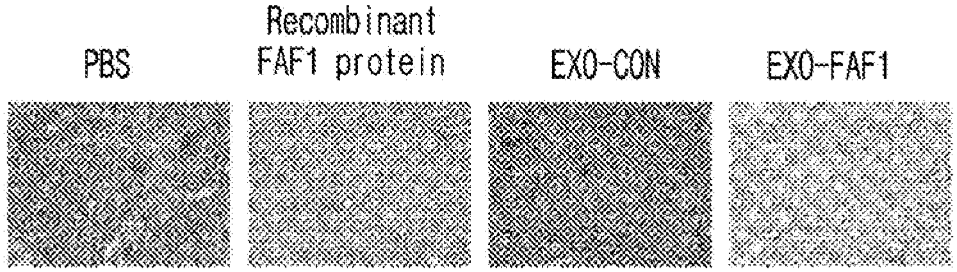

【Fig. 13a】
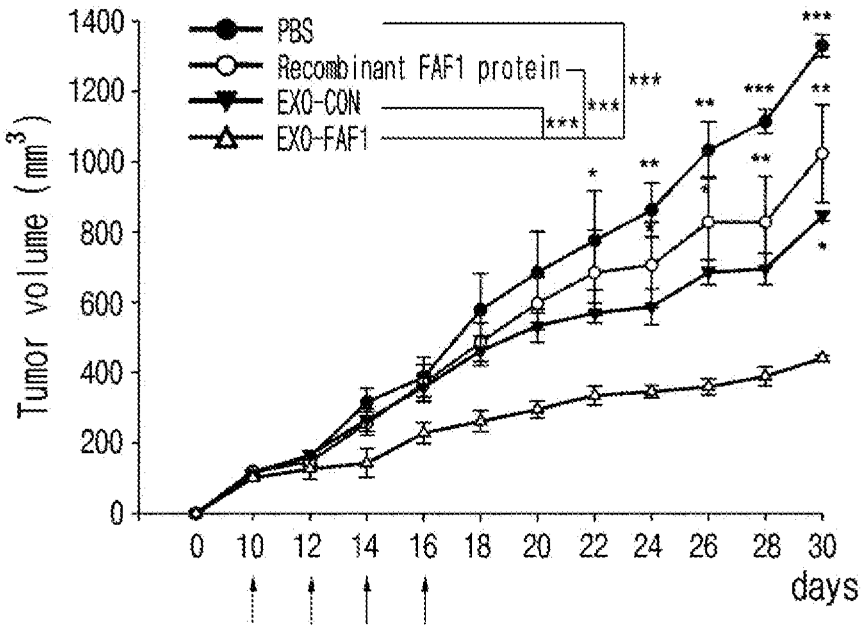
【Fig. 13b】
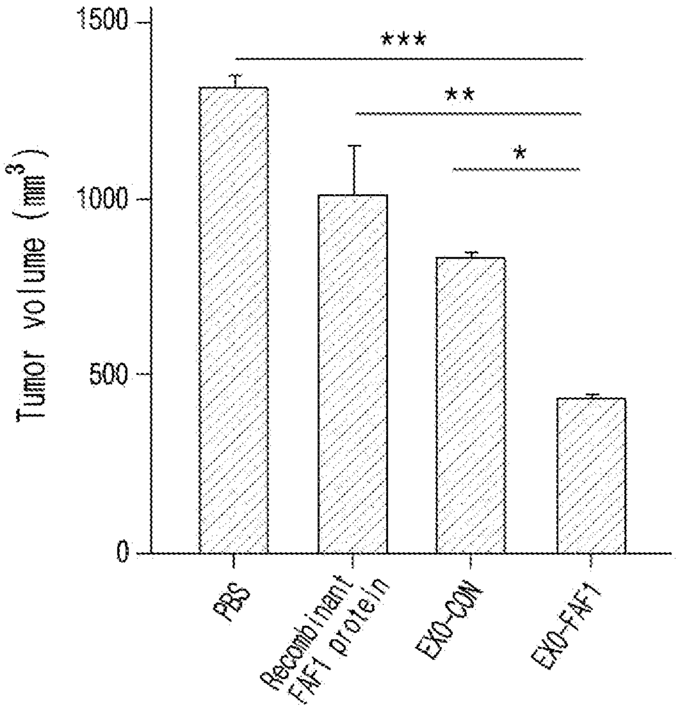

【Fig. 13c】
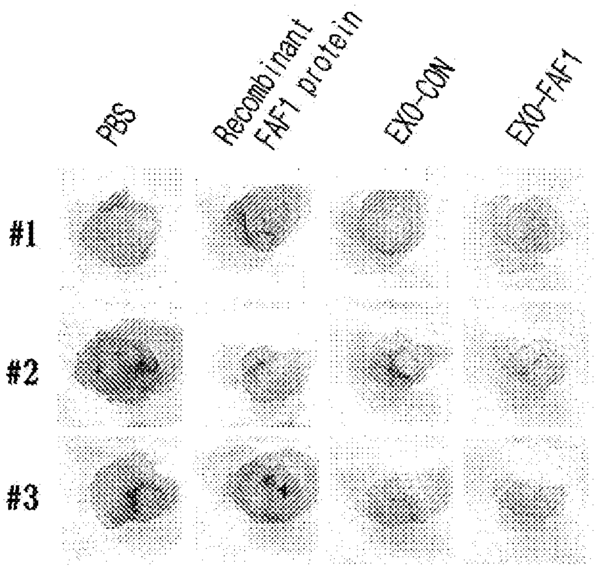
【Fig. 13d】
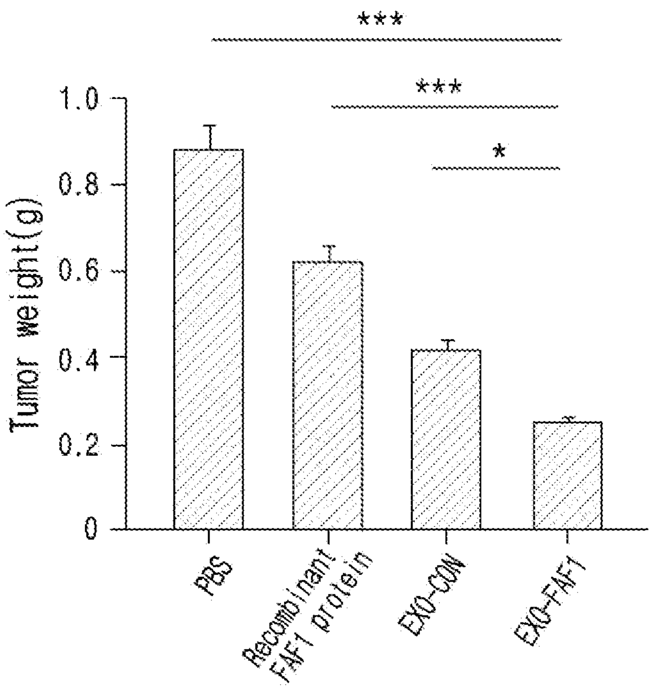

【Fig. 13e】
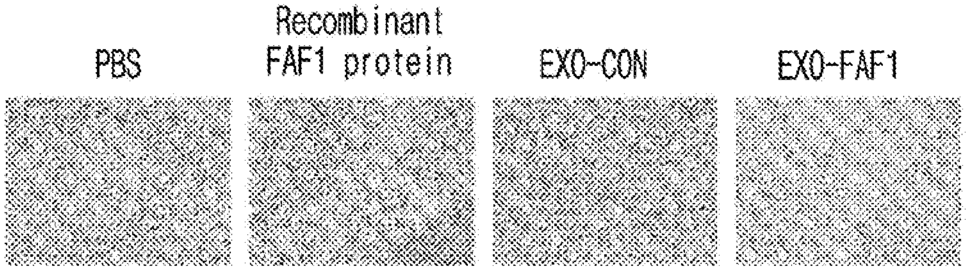
【Fig. 14a】
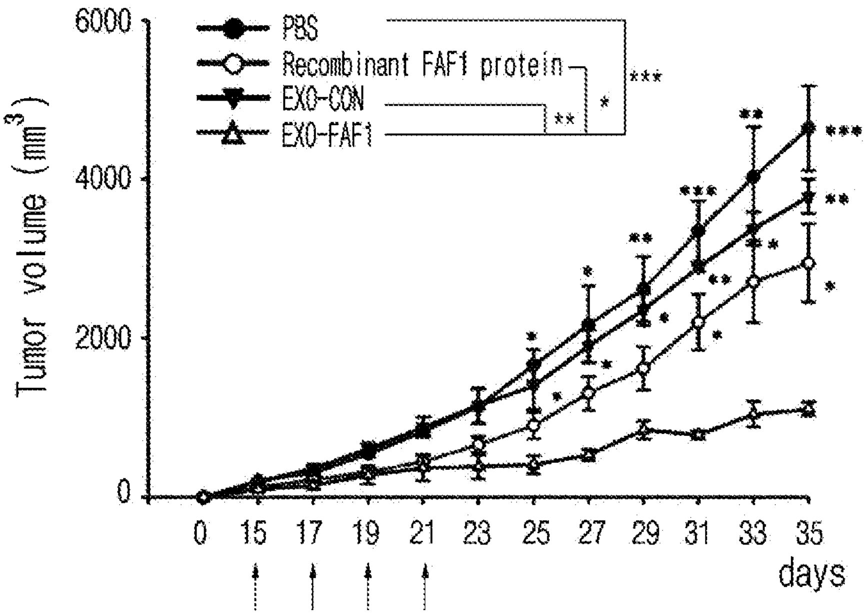

【Fig. 14b】
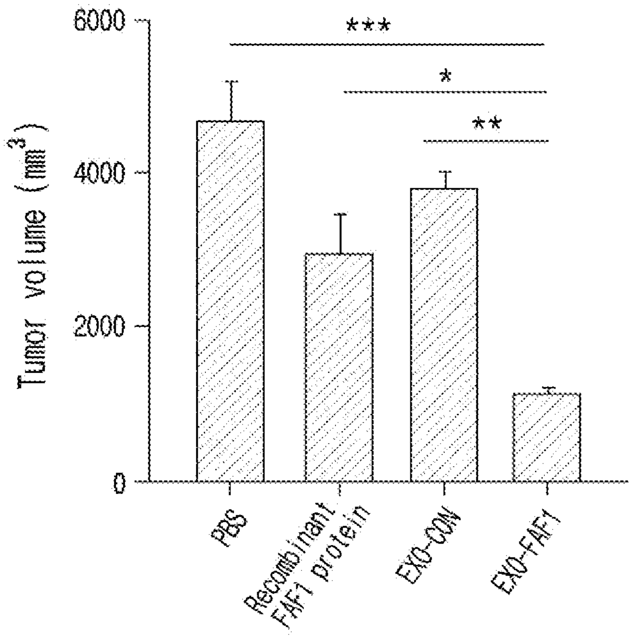
【Fig. 14c】
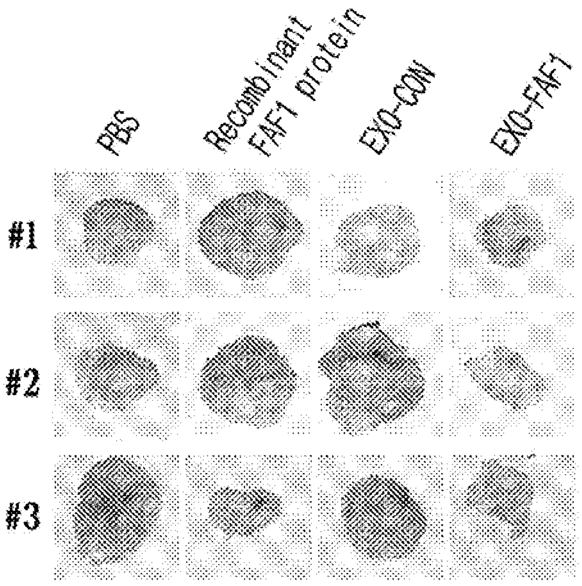

【Fig. 14d】
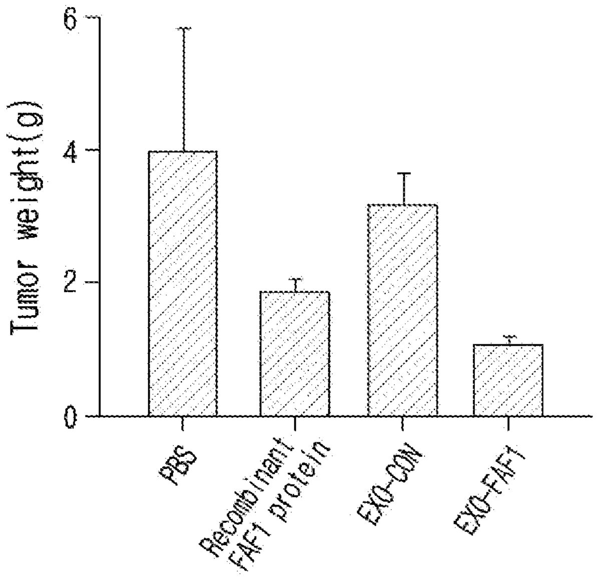
【Fig. 14e】
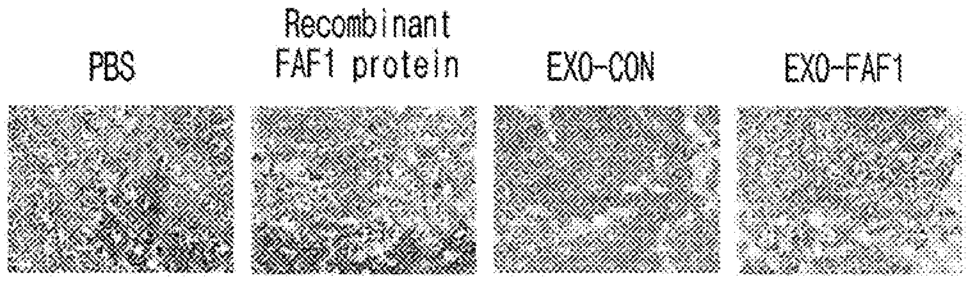

【Fig. 15a】
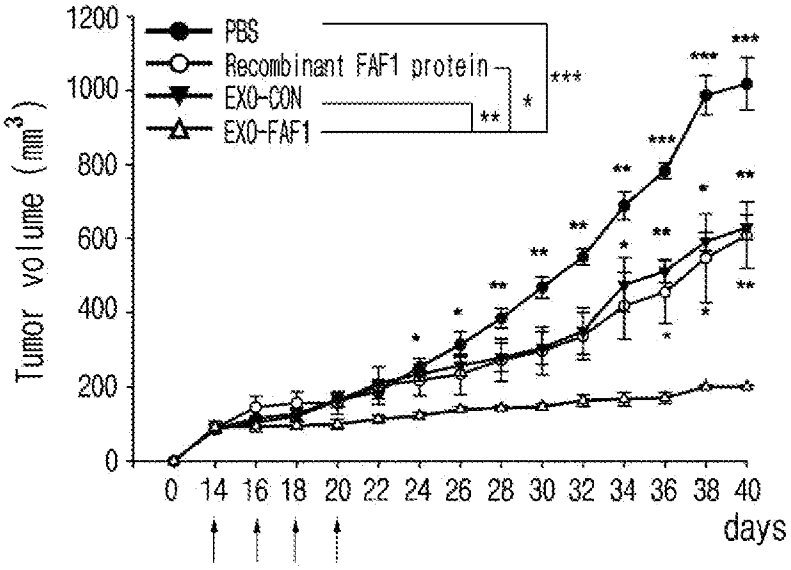
【Fig. 15b】
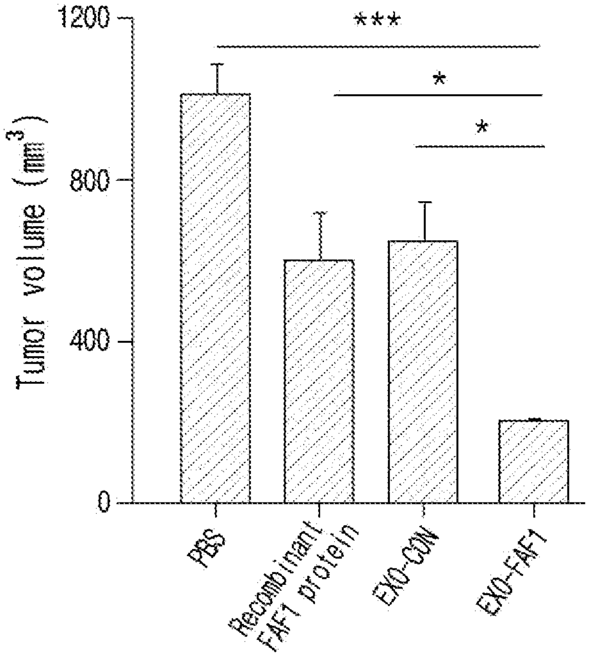

【Fig. 15c】
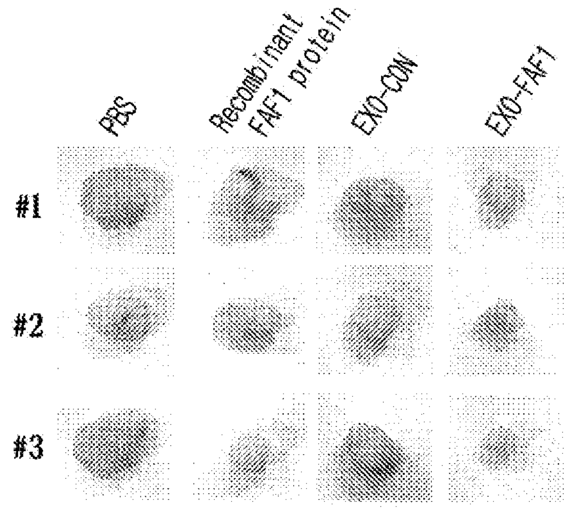
【Fig. 15d】
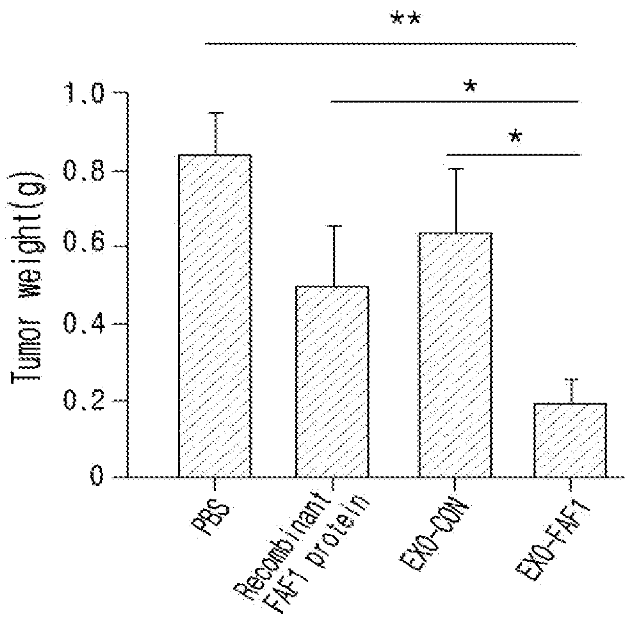

【Fig. 15e】
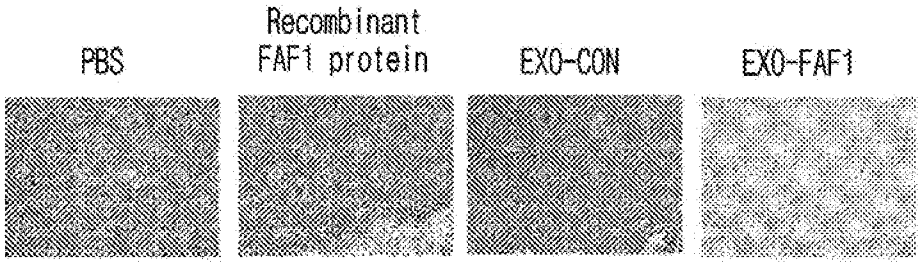
【Fig. 16a】
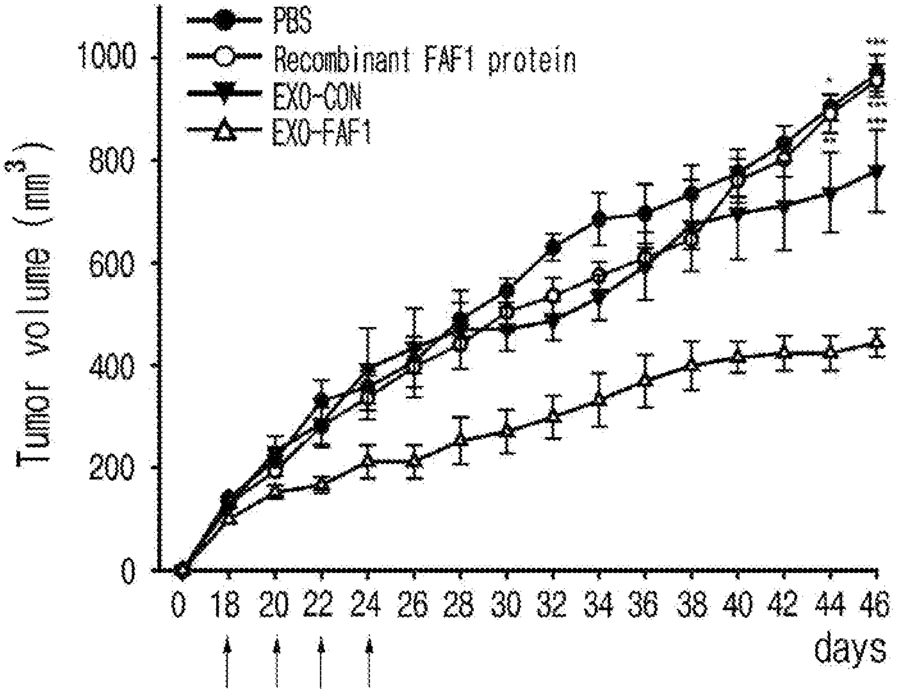

【Fig. 16b】
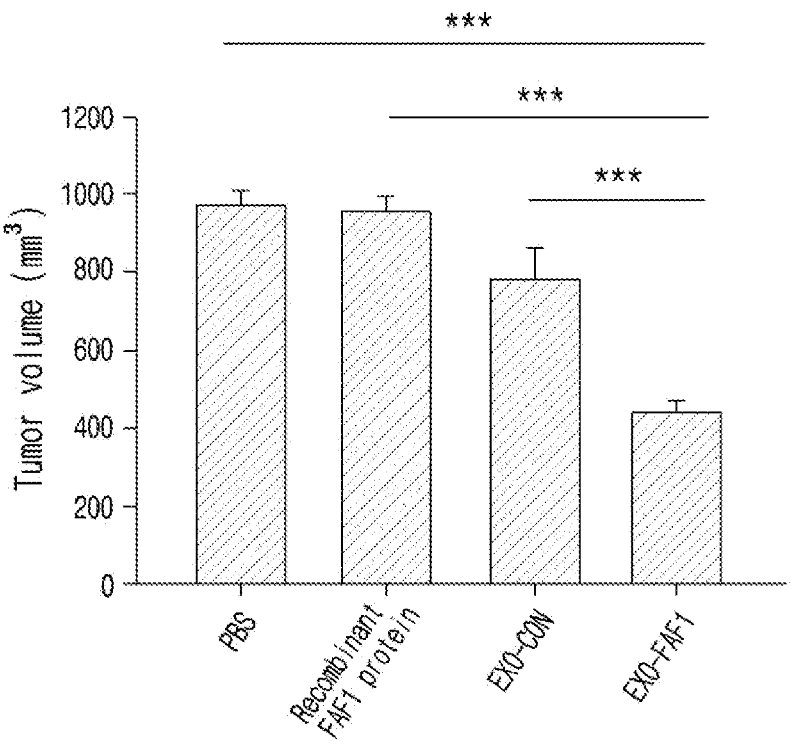
【Fig. 16c】
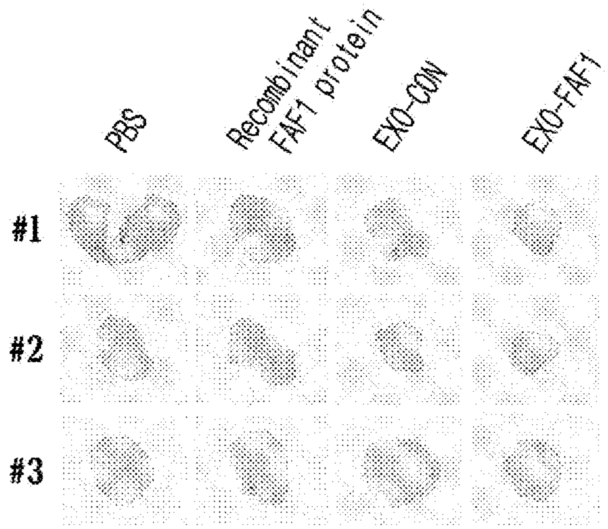

【Fig. 16d】
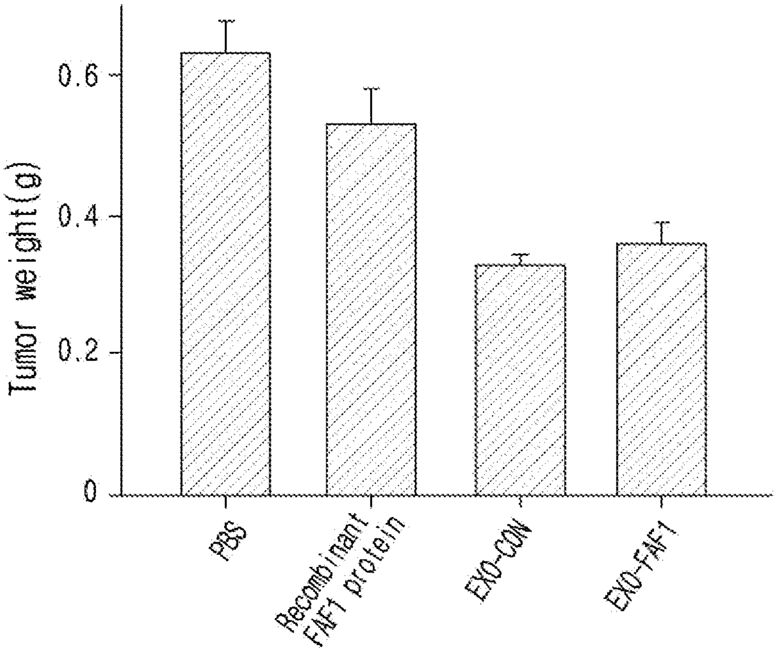
【Fig. 16e】
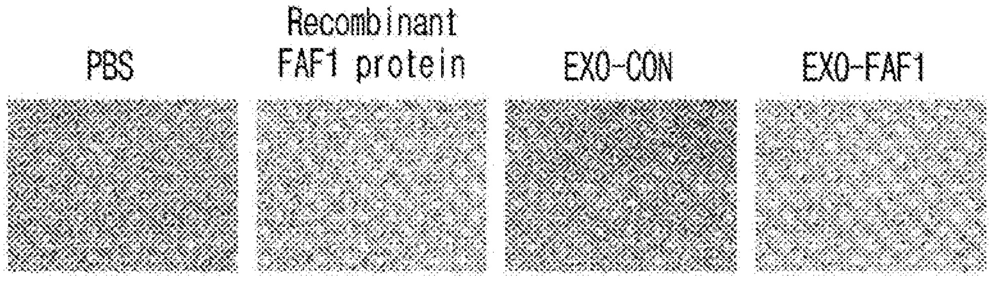

【Fig. 17a】
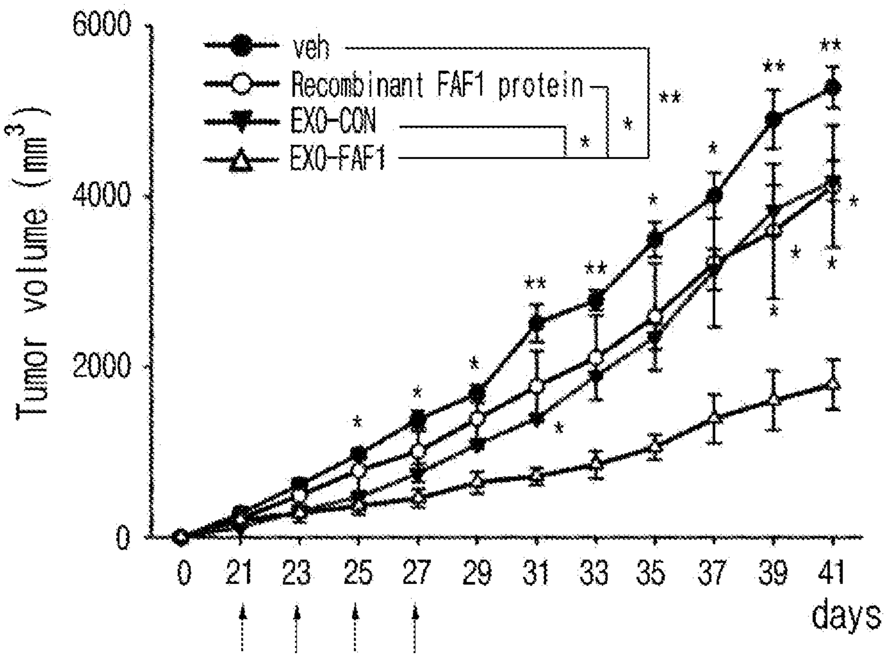
【Fig. 17b】
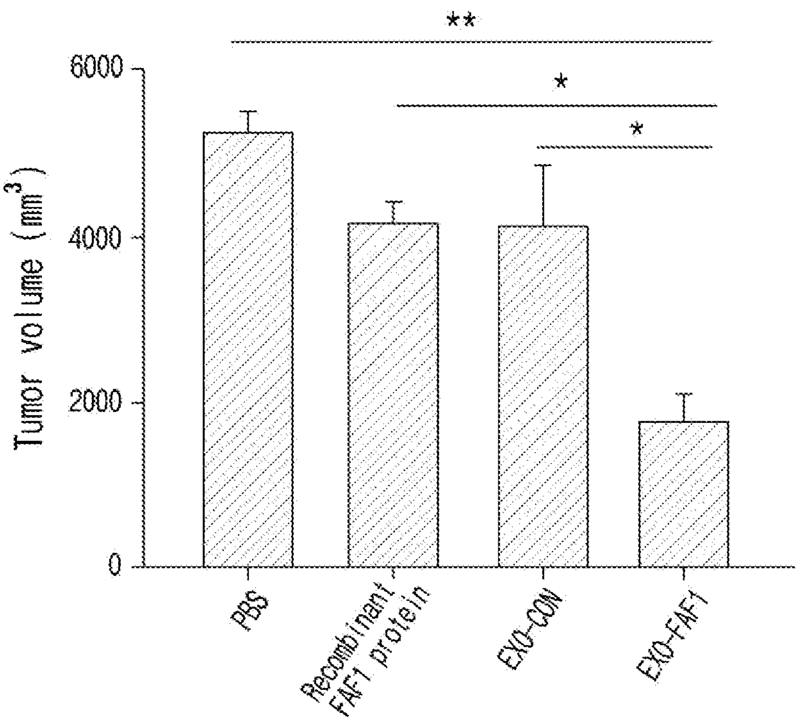

【Fig. 17c】
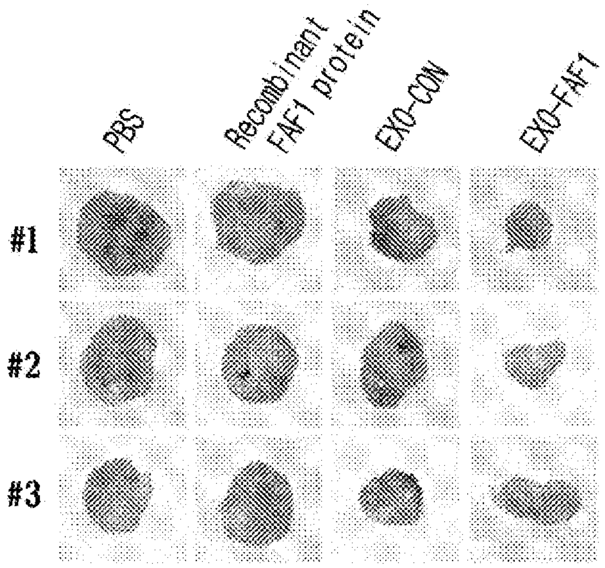
【Fig. 17d】
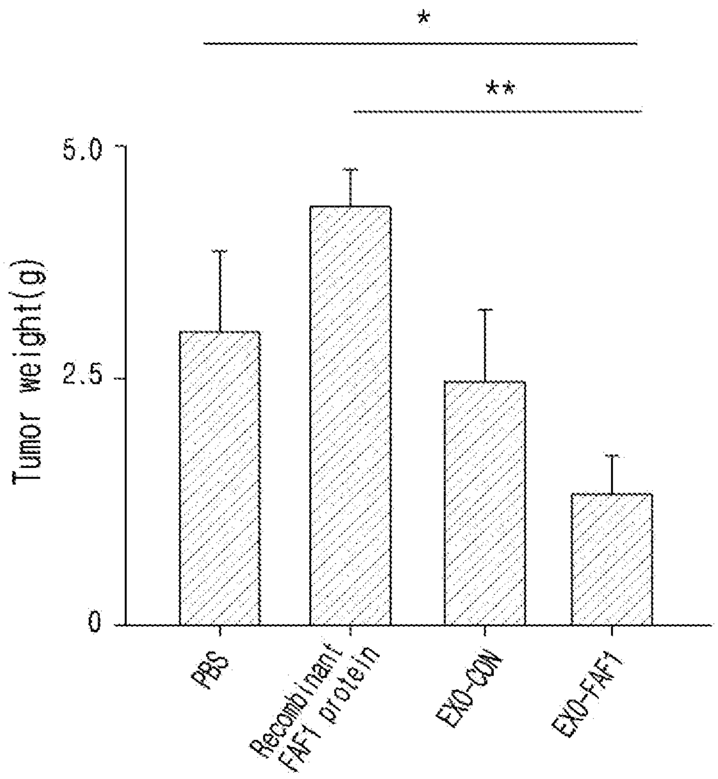

【Fig. 17e】
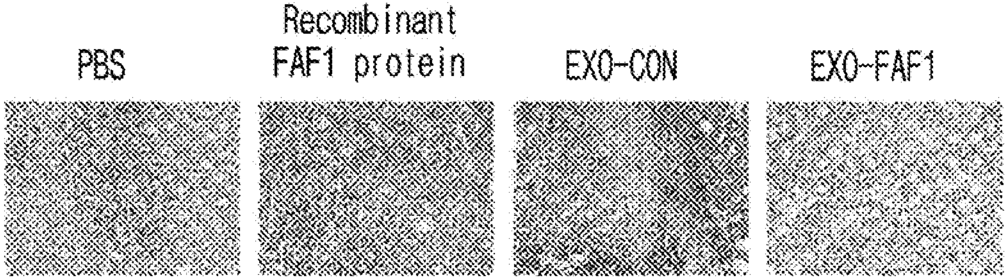

FAS-ASSOCIATED FACTOR 1 (FAF1)-LOADED EXOSOMES AND USE THEREOF AS ANTI-CANCER AGENT

CROSS REFERENCE TO RELATED APPLICATIONS

This application is a National Stage of International Application No. PCT/KR2022/004475 filed Mar. 30, 2022, claiming priority based on Korean Patent Application No. 10-2021-0040990 filed Mar. 30, 2021.

INCORPORATION BY REFERENCE OF SEQUENCE LISTING

The content of the electronically submitted sequence listing, file name: Q291360_SEQ_LIST_ST25.txt; size: 5,508 bytes; and date of creation: Sep. 20, 2023, filed herewith, is incorporated herein by reference in its entirety.

TECHNICAL FIELD

The present invention relates to FAF1-loaded exosomes, and a use thereof as an anti-cancer agent.

BACKGROUND ART

A tumor is a product of the disordered hyperproliferation of abnormal cells, and when such a tumor has destructive proliferative, invasive, and metastatic properties, the tumor is classified as a malignant tumor, that is, cancer. Cancer-related deaths take the first place for causes of death in Korea and are one of the most important causes of death in advanced countries. Until now, in an effort to treat cancer, surgical therapy was developed and used until the 1950s, radiation therapy in the 1960s, and anti-cancer drug therapy in the 1970s. In the 1980s, immunotherapy and gene therapy began to emerge owing to the radical development of basic science, particularly immunology and molecular biology, and many studies are currently ongoing, but it is still insufficient to achieve breakthroughs as existing therapies.

Fas (also known as Fas receptor, CD95, Apo1, or TNFRSF6) is a receptor having the best ability to kill cells among death receptors, and Fas and Fas ligand (Fas L) play an important role in apoptosis. When three Fas ligands bind to three Fas molecules, an adaptor protein called Fas-associated death domain (FADD) binds to a death domain (DD) of Fas. Then, when the death effector domain (DED) of the FADD is combined with the death effector domain (DED) of the inactive caspase-8 (also known as FLICE or MACH), the caspase-8 is activated, and these Fas, FADD, and caspase-8 form a Fas-death-inducing signaling complex (Fas-DISC), and eventually activate the effector caspase that causes cell death, thereby inducing cell death.

Fas-associated factor 1 (FAF1) is a protein associated with the Fas pathway and was found in mice (Chu et al., 1995; Becker et al., 1997) and quails (Frohlich et al., 1998) and humans (Ryu et al., 1999). These have high amino acid homology to each other, and the FAF1 in mice is composed of 649 amino acids, the FAF1 in quails is composed of 648 amino acids, and the FAF1 in humans is composed of 650 amino acids.

In previous studies on FAF1, the FAF1 has been found to have the ability to induce apoptosis, and the minimum region of induction is the 181-381 amino acid region of FAF1. It has been found that FAF1 is a member of Fas-DISC, and DISC is formed by the interaction of the DEDs of caspase-8 and FADD and the 181-381 amino acid region of FAF1, which is structurally similar to the DED (Ryu and Kim, 2003).

It has been reported that the expression level of FAF1 is lowered in various cancers including lung cancer, colon cancer, liver cancer, prostate cancer, brain cancer, and breast cancer (Feng et al., 2017), and the FAF1 protein is attracting attention as a tumor suppressor, and FAF1 is known to suppress tumors via NF-kB inhibition and suppress tumor metastases via TGF-β signals (Park et al., 2004; Park et al., 2007). In addition, it is known that FAF1 inhibits the proliferation of tumors by arresting the cell cycle of tumors at G2/M phase through Aurora-A inhibition (Jang et al., 2008). Korean Patent Laid-open Publication No. 10-2004-0101707 discloses that a fragment of a specific region of FAF1 has activities of inhibiting angiogenesis and tube formation, and cell proliferation, and thus, the fragment can be used as a tumor suppressor.

Extracellular vesicles were first discovered 50 years ago, and since then, it has been found that vesicles exist in all tested biological fluids, and it is known that cell lines in vitro release the vesicles in various ranges. Among the extracellular vesicles, exosome is a vesicle composed of a phospholipid bilayer and having a size of 50-200 nm, which is produced in a cell and secreted to the outside, and have been found to play an important role in intercellular communication through intercellular delivery of specific repertoires of nucleic acids (DNA and RNA), proteins, and lipids that are important for homeostasis. For example, exosomes are involved in basic physiological processes such as neurotransmission, antigen presentation, immune response, organ development, and reproductive ability, and also involved in some pathological disorders including cancer progression, cardiovascular disease, inflammation, and prion transmission.

Exosomes were first discovered in the process of releasing and removing intracellular proteins in the final stage of maturation of a red blood cell, leaving only hemoglobin in the red blood cell, and it was observed that these exosomes were released and secreted into the extracellular space, originating from specific compartments in the cell, called multivesicular bodies (MVBs), rather than being directly separated from a plasma membrane, in a study through an electron microscope. That is, when the multivesicular bodies fuse with the plasma membrane, such vesicles are released into the extracellular environment, which is called exosomes.

Many studies are being conducted on what molecular mechanism exosomes are made by, and various types of immune cells including B-lymphocytes, T-lymphocytes, dendritic cells, megakaryocytes, macrophages, and the like, and stem cells and tumor cells are known to produce and secrete exosomes. Although it has been reported that the production of exosomes is dependent or independent on the endosomal sorting complex required for transport (ESCRT), it is difficult to determine the exact mechanism.

Korean Patent Laid-open Publication No. 2004-0015508, as a related art, discloses a method in which a gene for a specific antigen is introduced into a cell line, and a protein of the introduced gene is stably expressed in the cell line and is released into the extracellular space through exosomes, and a method for using the exosomes as a vaccine. In addition, Korean Patent No. 10-2053065 relates to a pH-sensitive exosome composition using hyaluronic acid and doxorubicin, and discloses a method for preparing a pH-sensitive exosome using doxorubicin and a high molecular material chemically combining hyaluronic acid and 3-diethylamino propylamine, and a cancer cell killing effect of the exosome. In addition, Korean Patent Laid-open Publication No. 10-2018-0078173 relates to a novel exosome-based anti-cancer agent, and discloses a recombinant exosome in which a receptor tyrosine kinase and SIRP, which are phagocytosis promoting proteins, are presented on the surface thereof and a recombinant exosome including an asparaginase, a protein toxin, an antibody specific to a cancer antigen or a fragment of the antibody, a tumor suppressor gene or an anti-angiogenic factor, and the like, which are anti-cancer proteins. In addition, Korean Patent Application No. 10-2019-0059724 discloses a method for screening candidate drugs for treating neurodegenerative diseases using confirming that FAF1 is loaded in exosomes and secreted into the extracellular space, but no study results related to cancer cells have been reported.

By using exosomes, cargo materials are protected from the extracellular environment, resulting in longer half-lives and, optionally, entry into the target cell. However, not all proteins are loaded into exosomes as cargo materials, and even when loaded into exosomes, the loaded cargo materials do not enter all cells. Also, it is technically difficult to load large-sized high molecular proteins inside an exosome, and the effectiveness of the loaded protein may be significantly deteriorated when the protein is engineered for loading. It has been reported that FAF1 is spontaneously loaded into an exosome in a nerve cell, but whether the FAF1 loaded in the exosome enters the cell and functions properly varies with the type of cell, and there is a limitation in that this must be verified by experiments. Therefore, if it is confirmed that FAF1 delivery using exosomes functions properly in cancer cells and it is possible to mass-produce the FAF1-loaded exosomes, the FAF1-loaded exosomes may be applied as a tumor suppressor in various cancers.

Accordingly, in order to determine whether the FAF1 known as tumor suppression function is loaded into exosomes to deliver the same to various types of tumors and the FAF1 loaded in the exosomes can suppress tumors, the present inventors have isolated exosomes from cells in which FAF1 was overexpressed, checked whether FAF1 was spontaneously loaded in the isolated exosomes, confirmed that cancer cells were treated with the isolated FAF1-loaded exosomes and the colony formation was suppressed, and confirmed the effect of significantly inhibiting tumor growth compared with other control groups including groups treated with recombinant FAF1 proteins when the FAF1 protein-loaded exosomes were administered to various mouse cancer models to which cancer cells were transplanted, thereby completing the present invention.

DISCLOSURE OF THE INVENTION

Technical Problem

An object of the present invention is to provide a pharmaceutical composition for treating cancer, containing FAF1 protein-loaded exosomes as an active ingredient.

Another object of the present invention is to provide a method for producing FAF1 protein-loaded exosomes.

Still another object of the present invention is to provide a method for screening cancer therapeutic agents having decreased expression of FAF1.

Solution to Problem

To achieve the above objectives, the present invention provides a pharmaceutical composition for treating cancer, the composition containing FAF1 protein-loaded exosomes as an active ingredient.

In addition, the present invention provides a method for producing FAF1 protein-loaded exosomes, the method including the steps of: 1) introducing a polynucleotide encoding FAF1 protein into cells to obtain transformed cells; 2) culturing the transformed cells; and 3) isolating exosomes from the cultured cells.

In addition, the present invention provides a method for screening cancer therapeutic agents, the method including the steps of: 1) treating, with a test substance, cancer cells having decreased expression of FAF1; 2) measuring the level of the FAF1 protein in exosomes isolated from the cells in step 1); and 3) selecting the test substance in which the level of the FAF1 protein in step 2) is increased as compared with a control group which is not treated with the test substance.

Advantageous Effects of Invention

The present invention relates to Fas-associated factor 1 (FAF1) protein-loaded exosomes and a cancer treatment use thereof. The present inventors have isolated FAF1 protein-loaded exosomes from HEK 293 cells in which FAF1 known to have a tumor suppressive function is overexpressed, and have administered the FAF1 protein-loaded exosomes to a tumor model, in which pancreatic cancer cells (MIA PaCa-2), lung cancer cells (A549), colorectal cancer cells (HCT 116), liver cancer cells (Hep3B), breast cancer cells (MDA-MB-231), kidney cancer cells (Caki-1) and cervical cancer cells (HeLa cells) are transplanted into nude mice, through intratumoral injection, and have confirmed that there were significant tumor growth inhibitory effects as compared with a control group not treated with FAF1, and thus the FAF1-loaded exosomes of the present invention can be used as a therapeutic agent for various types of cancer.

BRIEF DESCRIPTION OF DRAWINGS

FIG. 1 shows a result of western blotting showing the amount of FAF1 loaded in exosomes isolated using an ultracentrifuge from HEK 293 cells in which FAF1 is overexpressed.

FIG. 2 shows a result of western blotting showing the amount of FAF1 loaded in exosomes isolated using an ultracentrifuge from HeLa cells in which FAF1 is overexpressed.

FIG. 3 shows a result of western blotting showing the amount of FAF1 loaded in exosomes isolated using Exoquick-TC™ from HEK 293 cells in which FAF1 is overexpressed.

FIG. 4 shows a result of western blotting showing the amount of FAF1 loaded in exosomes isolated using Exoquick-TC™ from HeLa cells in which FAF1 is overexpressed.

FIG. 5*a* shows photographs showing the effect of inhibiting the colony formation when MIA PaCa-2 cells are treated with exosomes isolated from HEK 293 cells, in which FAF1 is overexpressed.

FIG. 5*b* is a graph showing the number of colonies when MIA PaCa-2 cells are treated with exosomes isolated from HEK 293 cells in which FAF1 is overexpressed.

FIG. 6*a* shows photographs showing the effect of inhibiting the colony formation when A549 cells are treated with exosomes isolated from HEK 293 cells in which FAF1 is overexpressed.

FIG. 6*b* is a graph showing the number of colonies when A549 cells are treated with exosomes isolated from HEK 293 cells in which FAF1 is overexpressed.

FIG. 7*a* shows photographs showing the effect of inhibiting the colony formation when HCT 116 cells are treated with exosomes isolated from HEK 293 cells in which FAF1 is overexpressed.

FIG. 7*b* is a graph showing the number of colonies when HCT 116 cells are treated with exosomes isolated from HEK 293 cells in which FAF1 is overexpressed.

FIG. 8*a* shows photographs showing the effect of inhibiting the colony formation when Hep3B cells are treated with exosomes isolated from HEK 293 cells in which FAF1 is overexpressed.

FIG. 8*b* is a graph showing the number of colonies when Hep3B cells are treated with exosomes isolated from HEK 293 cells in which FAF1 is overexpressed.

FIG. 9*a* shows photographs showing the effect of inhibiting the colony formation when MDA-MB-231 cells are treated with exosomes isolated from HEK 293 cells in which FAF1 is overexpressed.

FIG. 9*b* is a graph showing the number of colonies when MDA-MB-231 cells are treated with exosomes isolated from HEK 293 cells in which FAF1 is overexpressed.

FIG. 10*a* shows photographs showing the effect of inhibiting the colony formation when HeLa cells are treated with exosomes isolated from HEK 293 cells in which FAF1 is overexpressed.

FIG. 10*b* is a graph showing the number of colonies when HeLa cells are treated with exosomes isolated from HEK 293 cells in which FAF1 is overexpressed.

FIG. 11*a* is a graph showing changes in tumor volume over time for MOCK, recombinant FAF1 protein, EXO-CON, and EXO-FAF1 groups when exosomes isolated from HEK 293 cells, in which FAF1 is overexpressed, are administered to nude mice xenotransplanted with MIA PaCa-2 cells.

FIG. 11*b* is a graph showing tumor volumes for MOCK, recombinant FAF1 protein, EXO-CON, and EXO-FAF1 groups when exosomes isolated from HEK 293 cells, in which FAF1 is overexpressed, are administered to nude mice xenotransplanted with MIAPaCa-2 cells.

FIG. 11*c* shows photographs of tumors for MOCK, recombinant FAF1 protein, EXO-CON, and EXO-FAF1 groups when exosomes isolated from HEK 293 cells, in which FAF1 is overexpressed, are administered to nude mice xenotransplanted with MIA PaCa-2 cells.

FIG. 11*d* is a graph showing tumor weights for MOCK, recombinant FAF1 protein, EXO-CON and EXO-FAF1 groups when exosomes isolated from HEK 293 cells, in which FAF1 is overexpressed, are administered to nude mice xenotransplanted with MIAPaCa-2 cells.

FIG. 11*e* shows photographs showing changes in cell morphology of tumor tissue for MOCK, recombinant FAF1 protein, EXO-CON, and EXO-FAF1 groups when exosomes isolated from HEK 293 cells, in which FAF1 is overexpressed, are administered to nude mice xenotransplanted with MIA PaCa-2 cells.

FIG. 12*a* is a graph showing changes in tumor volume over time for MOCK, recombinant FAF1 protein, EXO-CON, and EXO-FAF1 groups when exosomes isolated from HEK 293 cells, in which FAF1 is overexpressed, are administered to nude mice xenotransplanted with A549 cells.

FIG. 12*b* is a graph showing tumor volumes for MOCK, recombinant FAF1 protein, EXO-CON and EXO-FAF1 groups when exosomes isolated from HEK 293 cells, in which FAF1 is overexpressed, are administered to nude mice xenotransplanted with A549 cells.

FIG. 12*c* shows photographs of tumors for MOCK, recombinant FAF1 protein, EXO-CON, and EXO-FAF1 groups when exosomes isolated from HEK 293 cells, in which FAF1 is overexpressed, are administered to nude mice xenotransplanted with A549 cells.

FIG. 12*d* is a graph showing tumor weights for MOCK, recombinant FAF1 protein, EXO-CON, and EXO-FAF1 groups when exosomes isolated from HEK 293 cells, in which FAF1 is overexpressed, are administered to nude mice xenotransplanted with A549 cells.

FIG. 12*e* shows photographs showing changes in cell morphology of tumor tissue for MOCK, recombinant FAF1 protein, EXO-CON, and EXO-FAF1 groups when exosomes isolated from HEK 293 cells, in which FAF1 is overexpressed, are administered to nude mice xenotransplanted with A549 cells.

FIG. 13*a* is a graph showing changes in tumor volume over time for MOCK, recombinant FAF1 protein, EXO-CON, and EXO-FAF1 groups when exosomes isolated from HEK 293 cells, in which FAF1 is overexpressed, are administered to nude mice xenotransplanted with HCT 116 cells.

FIG. 13*b* is a graph showing tumor volumes for MOCK, recombinant FAF1 protein, EXO-CON, and EXO-FAF1 groups when exosomes isolated from HEK 293 cells, in which FAF1 is overexpressed, are administered to nude mice xenotransplanted with HCT 116 cells.

FIG. 13*c* shows photographs of tumors for MOCK, recombinant FAF1 protein, EXO-CON, and EXO-FAF1 groups when exosomes isolated from HEK 293 cells, in which FAF1 is overexpressed, are administered to nude mice xenotransplanted with HCT 116 cells.

FIG. 13*d* is a graph showing tumor weights for each group of MOCK, recombinant FAF1 protein, EXO-CON and EXO-FAF1 when exosomes isolated from HEK 293 cells, in which FAF1 is overexpressed, are administered to nude mice xenotransplanted with HCT 116 cells.

FIG. 13*e* shows photographs showing changes in cell morphology of tumor tissue for MOCK, recombinant FAF1 protein, EXO-CON, and EXO-FAF1 groups when exosomes isolated from HEK 293 cells, in which FAF1 is overexpressed, are administered to nude mice xenotransplanted with HCT 116 cells.

FIG. 14*a* is a graph showing changes in tumor volume over time for MOCK, recombinant FAF1 protein, EXO-CON, and EXO-FAF1 groups when exosomes isolated from HEK 293 cells, in which FAF1 is overexpressed, are administered to nude mice xenotransplanted with Hep3B cells.

FIG. 14*b* is a graph showing tumor volumes for each group of MOCK, recombinant FAF1 protein, EXO-CON and EXO-FAF1 when exosomes isolated from HEK 293 cells, in which FAF1 is overexpressed, are administered to nude mice xenotransplanted with Hep3B cells.

FIG. 14*c* shows photographs of tumors for MOCK, recombinant FAF1 protein, EXO-CON, and EXO-FAF1 groups when exosomes isolated from HEK 293 cells, in which FAF1 is overexpressed, are administered to nude mice xenotransplanted with Hep3B cells.

FIG. 14*d* is a graph showing tumor weights for MOCK, recombinant FAF1 protein, EXO-CON, and EXO-FAF1 groups when exosomes isolated from HEK 293 cells, in which FAF1 is overexpressed, are administered to nude mice xenotransplanted with Hep3B cells.

FIG. 14*e* shows photographs showing changes in cell morphology of tumor tissue for MOCK, recombinant FAF1 protein, EXO-CON, and EXO-FAF1 groups when exosomes isolated from HEK 293 cells, in which FAF1 is overexpressed, are administered to nude mice xenotransplanted with Hep3B cells.

FIG. 15*a* is a graph showing changes in tumor volume over time for MOCK, recombinant FAF1 protein, EXO-CON, and EXO-FAF1 groups when exosomes isolated from HEK 293 cells, in which FAF1 is overexpressed, are administered to nude mice xenotransplanted with MDA-MB-231 cells.

FIG. 15*b* is a graph showing tumor volumes for each group of MOCK, recombinant FAF1 protein, EXO-CON and EXO-FAF1 when exosomes isolated from HEK 293 cells, in which FAF1 is overexpressed, are administered to nude mice xenotransplanted with MDA-MB-231 cells.

FIG. 15*c* shows photographs of tumors for MOCK, recombinant FAF1 protein, EXO-CON, and EXO-FAF1 groups when exosomes isolated from HEK 293 cells, in which FAF1 is overexpressed, are administered to nude mice xenotransplanted with MDA-MB-231 cells.

FIG. 15*d* is a graph showing tumor weights for MOCK, recombinant FAF1 protein, EXO-CON, and EXO-FAF1 groups when exosomes isolated from HEK 293 cells, in which FAF1 is overexpressed, are administered to nude mice xenotransplanted with MDA-MB-231 cells.

FIG. 15*e* shows photographs showing changes in cell morphology of tumor tissue for each group of MOCK, recombinant FAF1 protein, EXO-CON, and EXO-FAF1 when exosomes isolated from HEK 293 cells, in which FAF1 is overexpressed, are administered to nude mice xenotransplanted with MDA-MB-231 cells.

FIG. 16*a* is a graph showing changes in tumor volume over time for MOCK, recombinant FAF1 protein, EXO-CON, and EXO-FAF1 groups when exosomes isolated from HEK 293 cells, in which FAF1 is overexpressed, are administered to nude mice xenotransplanted with Caki-1 cells.

FIG. 16*b* is a graph showing tumor volumes for MOCK, recombinant FAF1 protein, EXO-CON, and EXO-FAF1 groups when exosomes isolated from HEK 293 cells, in which FAF1 is overexpressed, are administered to nude mice xenotransplanted with Caki-1 cells.

FIG. 16*c* shows photographs of tumors for MOCK, recombinant FAF1 protein, EXO-CON, and EXO-FAF1 groups when exosomes isolated from HEK 293 cells, in which FAF1 is overexpressed, are administered to nude mice xenotransplanted with Caki-1 cells.

FIG. 16*d* is a graph showing tumor weights for MOCK, recombinant FAF1 protein, EXO-CON and EXO-FAF1 groups when exosomes isolated from HEK 293 cells, in which FAF1 is overexpressed, are administered to nude mice xenotransplanted with Caki-1 cells.

FIG. 16*e* shows photographs showing changes in cell morphology of tumor tissue for MOCK, recombinant FAF1 protein, EXO-CON, and EXO-FAF1 groups when exosomes isolated from HEK 293 cells, in which FAF1 is overexpressed, are administered to nude mice xenotransplanted with Caki-1 cells.

FIG. 17*a* is a graph showing changes in tumor volume over time for MOCK, recombinant FAF1 protein, EXO-CON, and EXO-FAF1 groups when exosomes isolated from HEK 293 cells, in which FAF1 is overexpressed, are administered to nude mice xenotransplanted with HeLa cells.

FIG. 17*b* is a graph showing tumor volumes for MOCK, recombinant FAF1 protein, EXO-CON, and EXO-FAF1 groups immediately before the enucleation of tumors when exosomes isolated from HEK 293 cells, in which FAF1 is overexpressed, are administered to nude mice xenotransplanted with HeLa cells.

FIG. 17*c* shows photographs of tumors for MOCK, recombinant FAF1 protein, EXO-CON, and EXO-FAF1 groups when exosomes isolated from HEK 293 cells, in which FAF1 is overexpressed, are administered to nude mice xenotransplanted with HeLa cells.

FIG. 17*d* is a graph showing tumor weights for the MOCK, Recombinant FAF1 protein, EXO-CON and EXO-FAF1 groups when exosomes isolated from HEK 293 cells, in which FAF1 is overexpressed, are administered to nude mice xenotransplanted with HeLa cells.

FIG. 17*e* shows photographs showing changes in cell morphology of tumor tissue for MOCK, recombinant FAF1 protein, EXO-CON, and EXO-FAF1 groups when exosomes isolated from HEK 293 cells, in which FAF1 is overexpressed, are administered to nude mice xenotransplanted with HeLa cells.

BEST MODE FOR CARRYING OUT THE INVENTION

Hereinafter, the present invention will be described in detail.

The present invention provides a pharmaceutical composition for treating cancer, the composition containing FAF1 protein-loaded exosomes as an active ingredient.

The FAF1 protein of the present invention includes an amino acid sequence represented by SEQ ID NO: 1.

FAF1 of the present invention constitutes a Fas-death-inducing signaling complex (Fas-DISC) and induces apoptosis. The FAF1 is known as a protein that activates several pathways and promotes apoptosis.

The FAF1 mediates cell necrosis through JNK-dependent mitochondrial dysfunction, is involved in cell proliferation by suppressing the G2/M phase in a cell cycle by negatively controlling Aurora-A, is involved in an ubiquitin-proteasome pathway by binding to an ubiquitinated protein and a valo sin containing protein (VCP) to regulate the degradation of protein, and unnecessary FAF1 is ubiquitinated through Parkin and degraded through the proteasome pathway.

In addition, the FAF1 is involved in various biochemical processes including apoptosis, inflammation, cell proliferation, and protein homeostasis. The FAF1 is a tumor suppressor, which plays a role in suppressing tumors via NF-κB inhibition, and also suppresses tumor metastases via TGF-β signals.

The exosomes of the present invention are small vesicles composed of two layers of phospholipid membrane secreted by cells, and are known to carry out signal transduction between cells, form disease-specific nucleic acids and proteins and release the same into body fluids, and play an important role in intercellular communication through the intercellular transduction of specific repertoires of nucleic acids, proteins, and lipids which are important in homeostasis. For example, the exosomes are involved in basic physiological processes such as neurotransmission, antigen presentation, immune response, organ development, and reproductive ability, and also involved in some pathological disorders including cancer progression, cardiovascular disease, inflammation, and prion transmission.

The exosomes are secreted into the extracellular environment after a late endosome, known as a multivesicular body (MVB) containing intralumenial vesicles (ILVs) fuses with the cell membrane. The multivesicular body may fuse with the cell membrane to release ILVs, whereas the multivesicular body may fuse with lysosome to degrade the contents. The materials present in the exosomes are not similar to the composition of cytoplasmic materials, and the exosomes may optionally contain RNA and proteins.

Although it has been reported that the production of exosomes is dependent or independent on the endosomal sorting complex required for transport (ESCRT), it is difficult to determine the exact mechanism. Cells secrete proteins, in which signal peptides are present, via the endoplasmic reticulum-Golgi complex. The vesicles containing the proteins in which signal peptides are present move toward the cell membrane, fuse with the cell membrane, and release the proteins into the extracellular space. However, proteins without signal peptides can be secreted via an alternative non-classical secretory pathway. When the proteins without signal peptides are secreted, the proteins are secreted either in the absence or presence of vesicles, and although the exact mechanism of the non-vesicular secretory pathway is unknown, some proteins are secreted via membrane pores and ATP-binding cassette transporters. Vesicular secretion is carried out via extracellular vesicles, including exosomes, and is carried out via vesicles with various sizes.

The exosomes may have an average diameter of 50 nm to 300 nm, but the present invention is not limited thereto.

Exosomes are nano-sized extracellular vesicles which are released by most types of cells and contain small RNAs, lipids, and proteins, and have several advantages over currently available synthetic drug delivery means. These advantages include the ability to overcome natural barriers, inherent cell targeting properties, improved permeability, maintenance effects, and biocompatibility. Based on the original function of delivering biological information, the application of exosomes as a therapeutic agent has been attracting attention.

The cancer is a cancer in which the expression of FAF1 is lowered.

The cancer includes, but is not limited to, cervical cancer, pancreatic cancer, liver cancer, lung cancer (including small cell lung carcinoma and non-small cell carcinoma), breast cancer, kidney cancer, colorectal cancer, squamous cell carcinoma of the head and neck, bladder cancer, prostate cancer, gastric cancer, endometrial cancer, brain cancer, ovarian cancer, testicular cancer, head cancer, neck cancer, skin cancer (including melanoma and basal carcinoma), mesothelial lining cancer, esophageal cancer, adrenal cancer, thyroid cancer, bone cancer, glioblastoma, mesothelioma, sarcoma, choriocarcinoma, cutaneous basal cell carcinoma, testicular seminoma, leukemia, and malignant lymphoma. In a preferred aspect, the cancer is pancreatic cancer, non-small cell lung cancer, colorectal cancer, liver cancer, triple negative breast cancer, kidney cancer, or cervical cancer.

The pharmaceutical composition of the present invention may include a carrier, a diluent, an excipient, or a mixture thereof, which are commonly used for pharmaceutical formulations. Any pharmaceutically acceptable carrier may be used as long as it is suitable for delivering the composition in the living body. Specifically, the carrier may be compounds described in Merck Index, 13th ed. Merck & Co. Inc., saline, sterilized water, Ringer's solution, dextrose solution, maltodextrin solution, glycerol, ethanol, or a mixture thereof. In addition, typical additives such as antioxidants, buffers, and bacteriostats may be added, if necessary.

When the pharmaceutical composition is formulated, diluents or excipients such as fillers, extenders, binders, wetting agents, disintegrants, and surfactants, which are commonly used, may be added.

The pharmaceutical composition of the present invention may be formulated into oral preparations or parenteral preparations. The oral preparations may include solid preparations and liquid preparations. The solid preparations may be tablets, pills, powders, granules, capsules, or troches, and the solid preparations may be prepared by adding at least one excipient to the composition. The excipient may be starch, calcium carbonate, sucrose, lactose, gelatin, or a mixture thereof. In addition, the solid preparations may include a lubricant, for example, magnesium stearate, and talc. Meanwhile, the liquid preparations may be suspensions, solutions, emulsions, or syrups. In this case, the liquid preparations may contain excipients such as wetting agents, sweeteners, fragrances, and preservatives.

The parenteral preparations may include injections, suppositories, powders for respiratory inhalation, spray aerosols, powders, creams, and the like. The injections may contain sterilized aqueous solutions, non-aqueous solvents, suspending agents, emulsifiers, and the like. In this case, as the non-aqueous solvents or the suspending agents, propylene glycol, polyethylene glycol, and vegetable oil such as olive oil, or injectable ester such as ethyl oleate, or the like may be used.

The pharmaceutical composition of the present invention may be administered orally or parenterally according to the desired method. Parenteral administration may include, but is not limited to, a method of intrabronchial inhalation, intraperitoneal, intrarectal, subcutaneous, intravenous, intramuscular, intrathoracic, or intratumoral injection. In a preferred aspect, the pharmaceutical composition of the present invention may be injected by the method of intratumoral injection.

The pharmaceutical composition may be administered in a pharmaceutically effective amount. This may vary with a type of disease, severity, drug activity, patient's sensitivity to drug, an administration time, an administration route, duration of treatment, drugs used simultaneously, and the like. However, for a desired effect, the amount of the active ingredient contained in the pharmaceutical composition according to the present invention may be 0.0001-1,000 mg/kg, specifically, 0.001-500 mg/kg. The administration may be performed once to several times a day.

The pharmaceutical composition of the present invention may be administered alone or in combination with other therapeutic agents. In combination administration, the administration may be performed sequentially or simultaneously.

In addition, the present invention provides a method for producing FAF1 protein-loaded exosomes, the method including the steps of:

1) introducing a polynucleotide encoding FAF1 protein into cells to obtain transformed cells;
2) culturing the transformed cells; and
3) isolating exosomes from the cells.

The cells in step 1) are any one or more cells selected from the group consisting of B-lymphocytes, T-lymphocytes, dendritic cells, megakaryocytes, macrophages, stem cells, tumor cells, and HEK293 cells, but are not limited thereto. In a preferred aspect, the cells are HEK 293 cells or HeLa cells.

The transduction may be performed by treating $5\times10^6$ to $7\times10^6$ of the cells with 5-10 μg of the 3×Flag-FAF1 plasmid and culturing the cells, and preferably treating $6.5\times10^6$ of the cells with 8 μg of the 3×Flag-FAF1 plasmid and culturing the cells.

The exosomes may be isolated by a method commonly used in the art for isolating the exosomes. Size exclusion chromatography, ion exchange chromatography, density gradient centrifugation, differential centrifugation, ultrafiltration, tangential flow filtration, exosome precipitation, total exosome isolation kit, immune-absorbent capture, affinity method, for example, affinity capture, affinity purification, immunoassay, microfluidic separation, or a combination thereof may be performed to isolate exosomes.

According to a specific embodiment of the present invention, the culture medium is collected and centrifuged at 300×g for 10 minutes, at 2,000 g for 10 minutes, and at 10,000 g for 30 minutes to separate the supernatant, the supernatant is filtered using a 0.2-μm filter, and centrifuged using an ultracentrifuge at 150,000×g for 70 minutes. The centrifuged supernatant is removed, the pellet is washed by adding PBS, and then centrifuged again for 150,000×g for 70 minutes to remove the supernatant, thereby isolating exosomes remaining in a lower layer.

The isolated exosomes may be stored at −20° C. and −80° C.

As used herein, the term "transformation" is a molecular biological technique in which a DNA chain fragment or plasmid etc. having an exogenous gene different from that of the original cell penetrates into the cell and binds to the DNA present in the original cell, thereby altering the genetic character of the cell.

The FAF1-loaded exosomes contain FAF1 proteins therein and serve as carriers for transporting FAF1 proteins to cancer cells or tissues.

The FAF1 proteins are secreted into the extracellular space via exosomes.

The extracellular-secreted FAF1 proteins may induce apoptosis in other cells.

The apoptosis is a kind of programmed cell death that may occur in multicellular organisms. The apoptosis leads to cell death due to changes in cell morphology and biochemical changes inside the cell. This process ends with cell swelling and cracking, cell membrane changes, chromatin condensation and chromosome cleavage, and the cell being engulfed by a phagocyte.

In contrast to necrosis, which is cell death caused by acute cellular injury, apoptosis does not harm organisms but confers advantages on the life cycle thereof. The formation of fingers and toes in the process of differentiation of human embryo is a representative example of apoptosis. In addition, apoptosis is an important mechanism in cell replacement, tissue remodeling, and removal of damaged cells.

Apoptosis occurs in two cases: one in order to eliminate unnecessary parts during the development and differentiation process, and the other in order to protect the other cells when the cell is severely damaged and likely to become cancerous. However, the cells that have problems in the process of apoptosis become cancer cells, and the cancer cells do not die, but rather gradually proliferate and grow through repeated division.

As used herein, the term "culture" refers to a method for growing cells or microorganisms under appropriately artificially controlled environmental conditions. In the present invention, a method for culturing the transformant may be performed using a method widely known in the art.

The medium refers to a known medium used for culturing animal cells, and may be selected from the group of commercially available serum-free media, protein-free media, and chemically defined media.

In addition, the present invention provides a method for screening cancer therapeutic agents, the method including the steps of:

1) treating, with a test substance, cancer cells having decreased expression of FAF1;
2) measuring the level of FAF1 protein in exosomes isolated from the cells in step 1); and
3) selecting the test substance in which the level of FAF1 protein in step 2) is increased as compared with a control group which is not treated with the test substance.

In the method, the cells of step 1) are not limited, but in a preferred aspect, MIA PaCa-2, A549, HCT 116, Hep3B, MDA-MB-231, Caki-1 or HeLa cells.

In the method, the test substance of step 1) means a substance that increases the expression of FAF1, and may be any one selected from the group consisting of a peptide, a protein, a non-peptide compound, a synthetic compound, a fermentation product, a cell extract, a plant extract, and an animal tissue extract, but is not limited thereto.

As a marker for selecting a candidate material used in the present invention, the level of FAF1 protein may be measured using a method known in the art. For example, antibodies that specifically detect the protein are commercially available, and may be used to detect the protein with Western blot, co-immunoprecipitation, immunofluorescence, enzyme-linked immunosorbent assay, and the like. By using such antibodies, the expression level of a specific protein may be specifically confirmed, but the present invention is not limited thereto.

An increase in the expression level of a specific protein may be selected as a candidate substance for a cancer therapeutic agent, as compared with a control group that is not treated with the test substance.

First, it was confirmed through an increase in the amount of FAF1 in the exosomes of HEK 293 cells and HeLa cells, in which FAF1 is overexpressed, that the overexpression of FAF1 in HEK 293 cells and HeLa cells increased the amount of FAF1 contained in the exosomes and made it possible to secrete FAF1 via the exosomes (see FIGS. 1 to 4). FAF1, an apoptosis-promoting factor, is a protein that can inhibit tumor formation. Accordingly, in order to confirm whether exosomes isolated from HEK 293 cells overexpressing FAF1 have the effect of suppressing tumor formation, tumor formation suppression tests were performed on MIA PaCa-2, A549, HCT 116, Hep3B, MDA-MB-231, or HeLa cells, and it was confirmed that the number of colonies formed when exosomes isolated from HEK 293 cells overexpressing FAF1 were treated was smaller than when exosomes isolated from HEK 293 cells not overexpressing FAF1 (see FIGS. 5*a*, 5*b*, 6*a*, 6*b*, 7*a*, 7*b*, 8*a*, 8*b*, 9*a*, 9*b*, 10*a*, and 10*b*). In addition, it was confirmed that the volume and weight of the tumor in the case of the FAF1-loaded exosomes were reduced by the intratumoral injection of exosomes isolated from HEK 293 cells overexpressing FAF1 into nude mice xenotransplanted with MIAPaCa-2, A549, HCT 116, Hep3B, MDA-MB-231, Caki-1, or HeLa cells, and it was confirmed that necrosis of cells occurred due to treatment of FAF1 (see FIGS. 11*a* to 11*e*, FIGS. 12*a* to 12*e*, FIGS. 13*a* to 13*e*, FIGS. 14*a* to 14*e*, FIGS. 15*a* to 15*e*, FIGS. 16*a* to 16*e*, and FIGS. 17*a* to 17*e*). The above results demonstrate that the loaded FAF1 can be secreted into the extracellular space via exosomes, the FAF1-loaded exosomes are properly delivered to target cancer cells, and the FAF1 can effectively suppress tumors, which means that the FAF1-loaded exosomes can be used as a cancer therapeutic agent.

Hereinafter, the present invention will be described in detail with reference to the following examples.

However, the following examples are only for illustrating the present invention, and the present invention is not limited thereto.

MODES FOR THE INVENTION

<Example 1> Isolation of Exosomes From HEK 293 Cells Overexpressing FAF1

<1-1> Cell Culture

HEK 293 cells, which are cell lines derived from human embryonic kidneys, were maintained while being subcultured once every two days under the conditions of 5% $CO_2$ and 37° C. in Dulbecco's modified Eagle's medium (DMEM, WelGENE, Korea) containing antibiotics, 10% fetal bovine serum (FBS, Atlas Biologicals, USA) and antibiotic-antimycotic (penicillin/streptomycin, GIBCO-BRL, USA).

<1-2> Intracellular Transduction

To overexpress FAF1 in cells, the 3×Flag tag-FAF1 plasmid (8 μg) was transduced into $6.5\times10^6$ cells.

Specifically, the cells were seeded into a 150-mm culture dish, and then the cells were cultured in the DMEM containing 10% FBS for 24 hours under the conditions of 5% $CO_2$ and 37° C. The 3×Flag tag-FAF1 was prepared by the method known previously (Yu et al., 2016). A total of 180 μL of a mixture was prepared at a ratio of DNA:BioT (Bioland scientific, USA)=1:1.5 using DMEM without FBS and antibiotics, and the mixture was reacted at room temperature for 5 minutes. The mixture was added to the cells cultured for 24 hours, and then the cells were reacted for 24 hours under the conditions of 5% $CO_2$ and 37° C.

<1-3> Exosome Isolation

<1-3-1> Isolation of Exosomes Using Exo-quick-TC™

Exosomes were isolated from cells transduced with the 3×Flag tag-FAF1 plasmid using Exo-quick-TC™ (System Biosciences, USA).

Specifically, 24 hours after the transduction, the cells were treated with DMEM (System Biosciences, USA) treated with 10% exosome-depleted FBS, and cultured for 48 hours. The medium of the cultured cells was collected and centrifuged at 3,000 rpm for 15 minutes to collect the supernatant from which the cell debris was removed. The collected medium (10 mL) was treated with 2 mL of Exo-quick buffer, shaken, and well mixed, so that the ratio of medium:Exo-quick buffer became 5:1. After overnight culture at 4° C., the process of centrifuging the medium at 1,500 g for 30 minutes was repeated twice to obtain exosomes.

<1-3-2> Isolation of Exosomes Using Ultracentrifuge

Exosomes were isolated from cells transduced with the 3×Flag tag-FAF1 plasmid using an ultracentrifuge (optima XE-100, BECKMAN Coulter, USA).

Specifically, 24 hours after the transduction, the cells were treated with DMEM without FBS and antibiotics and cultured again for 24 hours. The medium of the cultured cells was collected and centrifuged at 300 g for 10 minutes, 2,000 g for 10 minutes, and 10,000 g for 30 minutes to separate the supernatant, and the supernatant was filtered with a 0.2-μm syringe filter (BioFACT, Korea).

To isolate exosomes for use in in vitro and in vivo experiments, the supernatant was centrifuged at 150.000 g for 70 minutes with 45Ti rotor in the BECKMAN Coulter optima XE-100 ultracentrifuge, the supernatant was discarded, and the pellet was washed with PBS. The washed PBS was centrifuged again at 150.000 g for 70 minutes, the supernatant was then discarded, and the remaining was collected in an EP tube using PBS.

The isolated exosomes were stored at −20° C. and −80° C., and thawed at 4° C. before use.

<Example 2> Isolation of Exosomes from HeLa Cells Overexpressing FAF1

<2-1> Cell Culture

HeLa cells, which are derived from cervical cancer patients, were maintained while being subcultured once every two days under the conditions of 5% $CO_2$ and 37° C. in DMEM (WelGENE, Korea) containing antibiotics, 10% FBS (Atlas Biologicals, USA), and antibiotic-antimycotic (penicillin/streptomycin, GIBCOBRL, USA).

<2-2> Intracellular Transduction

To overexpress FAF1 in HeLa cells, the 3×Flag tag-FAF1 plasmid (8 μg) was transduced into $6.5\times10^6$ cells.

A specific experimental method is the same as in Example 1-2.

<2-3> Exosome Isolation

Exosomes were isolated from HeLa cells transduced with the 3×Flag tag-FAF1 plasmid using Exo-quick-TC™ or an ultracentrifuge.

A specific experimental method is the same as in Example 1-3.

<Example 3> Culture of Cancer Cell Lines

MIA PaCa-2 (pancreatic cancer cells), Hep3B (liver cancer cells), MDA-MB-231 (triple negative breast cancer cells), Caki-1 (kidney cancer cells), and HeLa (cervical cancer cells) were cultured in an incubator under the conditions of DMEM, 10% FBS, 1% antibiotic-antimycotic (penicillin/streptomycin, GIBCO BRL, USA), 5% $CO_2$, and 37° C., and subcultured once every three days. A549 (non-small cell lung cancer cells) and HCT 116 (colorectal cancer cells) were cultured in an incubator in the RPMI 1640 medium under the conditions of 10% FBS, 1% antibiotic-antimycotic, 5% $CO_2$, 37° C. and subcultured once every three days.

<Experimental Example 1> Confirmation of Increase in FAF1 in Exosomes when FAF1 is Overexpressed in HEK 293 Cells and HeLa Cells In order to find out whether more FAF1 enter exosomes when FAF1 is overexpressed in the HEK 293 cells and the HeLa cells, the expression level of FAF1 in exosomes isolated using the ultracentrifuge and Exo-quick-TC™ in the HEK 293 cells and HeLa cells transduced with the 3×Flag tag-FAF10 plasmid (8 μg) of Example 1 was confirmed by western blotting.

Specifically, in order to perform western blotting, 50 μL of a mammalian lysis buffer was added to the pellet from which the supernatant was removed and dissolved on ice for 30 minutes. A western blot kit (Amersham Biosciences, UK) was used to prepare 8-10% acrylamide gel, the dissolved pellet was mixed with 5 μL of SDS sample buffer, boiled for 3 minutes, and then put on the gel in a predetermined amount and applied a voltage of 80-100 V to separate the proteins in the pellet by size. The acrylamide gel containing the separated proteins was placed to overlap a nitrocellulose membrane and a current of 200 mA was applied for 2 hours to transfer the proteins to the nitrocellulose membrane. The nitrocellulose membrane to which the protein was transferred was blocked with nonfat dry milk, the FAF1 antibodies were attached thereto, and then the secondary antibodies were attached thereto, the amount of the FAF1 protein was confirmed by the western blot detection kit (AbFrontier, Korea) and ChemiDoc-It Imaging System (UVP, USA).

When exosomes were isolated using the ultracentrifuge, the expression of FAF1 was slightly increased in the exosomes isolated from HEK 293 cells in which FAF1 was overexpressed, as compared to the exosomes isolated from HEK 293 cells in which FAF1 was not overexpressed (FIG.

1). In the case of HeLa cells, rarely seen was the expression of FAF1 in the exosomes isolated from cells in which FAF1 was not overexpressed and cells in which FAF1 was overexpressed (FIG. 2).

When exosomes were isolated using Exo-quick-TC™, the expression level of FAF1 in the exosomes isolated from cells overexpressing FAF1 was significantly increased in HEK 293 cells (FIG. 3), and FAF1 was not seen in the exosomes isolated from cells overexpressing FAF1 in HeLa cells, but it was confirmed through Flag, which is a tag protein, that the amount of FAF1 was increased (FIG. 4).

The method for isolating exosomes using Exo-quick-TC™ is simpler than the method for using an ultracentrifuge, and has the advantage of reducing time, but has the disadvantage of causing contamination during the isolation process. In addition, since the method using the ultracentrifuge may isolate the exosomes having higher purity, the present inventors isolated the exosomes using the ultracentrifuge in the following experimental examples in order to confirm the effect of pure exosomes.

<Experimental Example 2> Confirmation of In Vitro Anti-Tumor Effect of Exosomes Isolated from HEK 293 Cells Overexpressing FAF1

By using exosomes isolated from HEK 293 cells overexpressing FAF1, the ability to inhibit the colony formation was evaluated in the cell lines of pancreatic cancer, non-small cell lung cancer, liver cancer, and cervical cancer.

Specifically, HEK 293 cells transduced with 3×Flag tag-FAF1 (0 or 8 μg) were cultured for 24 hours, cultured in the FBS- and antibiotic-free medium for 24 hours in order to promote exosome secretion, and then the medium was collected and exosomes were isolated using an ultracentrifuge (optima XE-100, BECKMAN Coulter). The isolated exosomes were quantified using a spectrophotometer (MECASYS, Korea). To see the in vitro effect of inhibiting the tumor colonies of FAF1-loaded exosomes in MIA PaCa-2, A549, HCT 116, Hep3B, MDA-MB-231 or HeLa cell lines, the MIA PaCa-2, Hep3B or HeLa cells were seeded into 6-well plate at 100 cells, and the A549, HCT116 and MDA-MB-231 cells were seeded at 200 cells. After 24 hours, the cells were treated with exosomes without loading FAF1 (exosome control: EXO-CON) and FAF1-loaded exosomes (EXO-FAF1). In the case of MIA PaCa-2, exosomes were measured by a spectrophotometer (MECASYS, Korea), the cells were treated with 6 μg of the exosomes, and then cultured for 12 days; in the case of A549, exosomes were measured by NTA, the cells were treated with $3\times10^{8}$ exosomes, and then cultured for 10 days; in the case of HCT 116, exosomes were measured by NTA, the cells were treated with $3.16\times10^{9}$ exosomes, and then cultured for 10 days; in the case of Hep3B, exosomes were measured by the spectrophotometer (MECASYS, Korea), the cells were treated with 12 μg of the exosomes, and then cultured for 7 days; in the case of MDA-MB_231, exosomes were measured by NTA, the cells were treated with $8.4\times10^{9}$ exosomes, and then cultured for 12 days; and in the case of HeLa, exosomes were measured by NTA, the cells were treated with $1.65\times10^{10}$ exosomes, and then cultured for 10 days. The medium was replaced with a fresh medium once every 3 days, and when the medium was replaced, the cells were treated with exosomes according to the respective concentrations. After completion of the experiments, the number of stained colonies was measured by washing with PBS, treating with 1 mL of methanol for 20 minutes, and treating with 1 mL of the crystal violet solution (SIGMA-ALDRICH, USA) for 5 minutes.

<2-1> Confirmation of Ability to Inhibit Colony Formation in Pancreatic Cancer In order to verify the ability to inhibit the colony formation of the anti-tumor effects of FAF1-loaded exosomes in pancreatic cancer, MIA PaCa-2 cells, which are the pancreatic cancer cell lines, were treated with the FAF1-loaded exosomes, and then checked.

As a result, as shown in FIGS. 5a and 5b, it was confirmed that the least number of colonies were formed in the group treated with EXO-FAF1. By confirming with the figures, it was confirmed that EXO-FAF1 decreased in the colony formation by 24.2±7.27% compared to EXO-CON and by 26.2±7.08% compared to MOCK.

The above results suggest that FAF1-loaded exosomes suppress tumor formation in pancreatic cancer.

<2-2> Confirmation of Ability to Inhibit Colony Formation in Non-Small Cell Lung Cancer In order to verify the anti-tumor effects of FAF1-loaded exosomes in non-small cell lung cancer, A549 cells, which are non-small cell lung cancer cell lines, were treated with FAF1-loaded exosomes, and then, the ability to inhibit the colony formation was confirmed.

As a result, as shown in FIGS. 6a and 6b, it was confirmed that the least number of colonies were formed in the group treated with EXO-FAF1. It was confirmed that EXO-FAF1 decreased in the colony formation by 46.9±12.88% compared to EXO-CON and by 42.7±13.91% compared to MOCK.

The above results suggest that FAF1-loaded exosomes suppress tumor formation in non-small cell lung cancer.

<2-3> Confirmation of Ability to Inhibit Colony Formation in Colorectal Cancer In order to verify the anti-tumor effects of FAF1-loaded exosomes in colorectal cancer, HCT 116 cells, which are colorectal cancer cell lines, were treated with FAF1-loaded exosomes, and then, the ability to inhibit the colony formation was confirmed.

As a result, as shown in FIGS. 7a and 7b, it was confirmed that the least number of colonies were formed in the group treated with EXO-FAF1. It was confirmed that EXO-FAF1 decreased in the colony formation by 23.0±9.07% compared to EXO-CON and by 30.9±8.14% compared to MOCK.

The above results suggest that the FAF1-loaded exosomes suppress tumor formation in colorectal cancer.

<2-4> Confirmation of Ability to Inhibit Colony Formation in Liver Cancer

In order to verify the anti-tumor effects of FAF1-loaded exosomes in liver cancer, Hep3B cells, which are liver cancer cell lines, were treated with FAF1-loaded exosomes, and then, the ability to inhibit the colony formation was confirmed.

As a result, as shown in FIGS. 8a and 8b, it was confirmed that the least number of colonies were formed in the group treated with EXO-FAF1. It was confirmed that EXO-FAF1 decreased in the colony formation by 50.6±10.21% compared to EXO-CON and by 46.1±11.15% compared to MOCK.

The above results suggest that the FAF1-loaded exosomes suppress tumor formation in liver cancer.

<2-5> Confirmation of Ability to Inhibit Colony Formation in Triple Negative Breast Cancer In order to verify the ability to inhibit the colony formation of the anti-tumor effects of FAF1-loaded exosomes in triple negative breast cancer, MDB-MB-231 cells, which are the triple negative breast cancer cell lines, were treated with the FAF1-loaded exosomes, and then checked.

As a result, as shown in FIGS. 9*a* and 9*b*, it was confirmed that the least number of colonies were formed in the group treated with EXO-FAF1. By confirming with the figures, it was confirmed that EXO-FAF1 decreased in the colony formation by 43.8±10.40% compared to EXO-CON and by 59.3±7.59% compared to MOCK.

The above results suggest that the FAF1-loaded exosomes suppress tumor formation in triple negative breast cancer.

<2-6> Confirmation of Ability to Inhibit Colony Formation in Cervical Cancer

In order to verify the ability to inhibit the colony formation of the anti-tumor effects of FAF1-loaded exosomes in cervical cancer, HeLa cells, which are the cervical cancer cell lines, were treated with the FAF1-loaded exosomes, and then checked.

As a result, as shown in FIGS. 10*a* and 10*b*, it was confirmed that the least number of colonies were formed in the group treated with EXO-FAF1. By confirming with the figures, it was confirmed that EXO-FAF1 decreased in the colony formation by 38.4±6.45% compared to EXO-CON and by 38.0±6.49% compared to MOCK.

The above results suggest that the FAF1-loaded exosomes suppress tumor formation in cervical cancer.

<Experimental Example 3> Confirmation of In Vivo Anti-Tumor Effect of Exosomes Isolated from HEK 293 Cells Overexpressing FAF1 in Tumor Xenograft Animal Model To see the in vivo effect of suppressing tumor of exosomes isolated from HEK293 cells overexpressing FAF1, 2-7×$10^6$ of each of MIA PaCa-2, A549, HCT 116, Hep3B, MDA-MB-231, Caki-1, and HeLa cell lines were mixed with 100 μL of PBS and 100 μL of matrigel (Corning Life Science, USA), and then xenotransplanted to the dorsal region of an 8-week-old male BALB/cSLC nu/nu mouse (Central Lab. Animal Inc., Korea) through a 26 G syringe. Tumor volume was calculated based on (long axis)×(short axis)$^2$×0.5. When the tumor volume reached 80-140 $mm^3$, PBS, recombinant FAF1 (AngioLab, Korea), EXO-CON, and EXO-FAF1 were injected to mice four times in total once every two days through intratumoral injection, respectively. The tumor volume of the MIA PaCa-2 cell line was measured up to 43 days, the tumor volume of the A549 cell line was measured up to 48 days, the tumor volume of the HCT 116 cell line was measured up to 30 days, the tumor volume of the Hep3B cell line was measured up to 35 days, the tumor volume of the MDA-MB-231 cell line was measured up to 40 days, the tumor volume of the Caki-1 cell line was measured up to 46 days, and the tumor volume of the HeLa cell line was measured up to 41 days. On the last day, after the mice were euthanized, the tumor was enucleated and weighed, and the inside of the tumor was examined through H&E staining.

The extracted tissue for H&E staining was stored in a formalin solution. After 24 hours, dehydration was performed for 20 minutes in 70% ethanol, dehydration was performed twice for 20 minutes in 95% ethanol, and finally, dehydration was performed twice in 100% ethanol for 20 minutes. Then, xylene and paraffin reactions were respectively performed for 3 hours using a tissue processor (Leica, Germany). To cut the tissue sections, the tissue was hardened in paraffin and cut to a thickness of 5 μm using a microtome, and the section was placed on a glass slide. Before staining began, the reaction was performed at 60° C. for 20 minutes using a slide warmer. Next, the reaction was performed in xylene three times for 3 minutes and 30 seconds. After the reaction was performed twice in 100% ethanol, and performed in 95%, 80%, and 70% ethanol in order once, for 3 minutes and 30 seconds each. Then, washing was performed under running water for 3 minutes. Next, the reaction was performed in hematoxylin for 5 minutes, followed by washing for 10 minutes HCl for 4 seconds, 1% ammonia for 10 seconds, washing for 5 minutes, and eosin for 1 minute and 10 seconds in order. Then, the slide was put in 70% ethanol and 85% ethanol in order for 1 minute and 30 seconds, each and then the reaction was performed twice in 100% ethanol for 1 minute and 30 seconds. After the ethanol reaction, a solution in which 100% ethanol and xylene were mixed in a ratio of 1:1 was reacted for 1 minute and 30 seconds. Finally, the reaction was performed with xylene for 3 minutes, and then again with fresh xylene for 4 minutes. The slide was covered with a glass cover using Shandon™ Synthetic Mountant (Thermo Scientific, USA). After staining was completed, it was observed through a microscope.

<3-1> Evaluation of Efficacy in Pancreatic Cancer Xenotransplanted Animal Models MIA PaCa-2 cells, which are pancreatic cancer cell lines, were xenotransplanted into immunodeficient nude mice to confirm whether FAF1-loaded exosomes have the ability to suppress the tumor formation.

As a result, as shown in FIGS. 11*a* and 11*b*, it was confirmed that the tumor volume decreased by 60.46±13.33% in the group treated with FAF1-loaded exosomes compared with the group treated with PBS, by 55.40±15.04% compared with the group treated with EXO-CON, and by 59.71±13.58% compared with the group treated with recombinant FAF1 (AngioLab, Korea). In addition, as shown in FIGS. 11*c* and 11*d*, it was confirmed that tumor weight decreased by 52.55±12.13% in the group treated with FAF1-loaded exosomes compared with the group treated with PBS, by 46.74±13.61% compared with the group treated with EXO-CON, and by 45.28±13.98% compared with the group treated with recombinant FAF1 (AngioLab, Korea).

In addition, as a result of observing the cell morphology of the tumor tissue through H&E staining, as shown in FIG. 11*e*, the cytoplasm size of the tumor tissue of the HEK Exo-FAF1 group was smaller than those of the MOCK group, the recombinant FAF1 group, and the HEK Exo-CON group, and thus it was confirmed that the cell necrosis occurred due to the treatment of HEK Exo-FAF1.

The above results demonstrate that FAF1 through exosomes also suppresses tumor formation in vivo.

<3-2> Evaluation of Efficacy in Non-small Cell Lung Cancer Xenotransplanted Animal Models A549 cells, which are non-small cell lung cancer cell lines, were xenotransplanted into immunodeficient nude mice to confirm whether FAF1-loaded exosomes have the ability to suppress the tumor formation.

As a result, as shown in FIGS. 12*a* and 12*b*, it was confirmed that the tumor volume decreased by 75.45±9.89% in the group treated with FAF1-loaded exosomes compared with the group treated with PBS, by 72.77±10.97% compared with the group treated with EXO-CON, and by 75.14±10.01% compared with the group treated with recombinant FAF1 (AngioLab, Korea). In addition, as shown in FIGS. 12*c* and 12*d*, it was confirmed that the tumor weight decreased by 59.07±13.88% in the group treated with FAF1-loaded exosomes compared with the group treated with PBS, by 61.31±13.12% compared with the group treated with EXO-CON, and by 63.19±12.48% compared with the group treated with recombinant FAF1 (AngioLab, Korea). In addition, as shown in FIG. 12*e*, it was confirmed that necrosis occurred inside the tumor of the group treated with EXO-FAF1.

<3-3> Evaluation of Efficacy in Colorectal Cancer Xenotransplanted Animal Models HCT 116 cell lines, which are colorectal cancer cell lines, were xenotransplanted into immunodeficient nude mice to confirm whether FAF1-loaded exosomes have the ability to suppress the tumor formation.

As a result, as shown in FIGS. 13*a* and 13*b*, it was confirmed that the tumor volume decreased by 66.87±7.62% in the group treated with FAF1-loaded exosomes compared with the group treated with PBS, by 47.87±12.00% compared with the group treated with EXO-CON, and by 56.93±9.91% compared with the group treated with recombinant FAF1 (AngioLab, Korea). In addition, as shown in FIGS. 13*c* and 13*d*, it was confirmed that the tumor weight decreased by 71.88±5.66% in the group treated with FAF1-loaded exosomes compared with the group treated with PBS, by 40.12±12.05% compared with the group treated with EXO-CON, and by 60.09±8.03% compared with the group treated with recombinant FAF1 (AngioLab, Korea). In addition, as shown in FIG. 13*e*, it was confirmed that necrosis occurred inside the tumor of the group treated with EXO-FAF1.

<3-4> Evaluation of Efficacy in Liver Cancer Xenotransplanted Animal Models

Hep3B cell lines, which are liver cancer cell lines, were xenotransplanted into immunodeficient nude mice to confirm whether FAF1-loaded exosomes have the ability to suppress the tumor formation.

As a result, as shown in FIGS. 14*a* and 14*b*, it was confirmed that the tumor volume decreased by 76.16±11.61% in the group treated with FAF1-loaded exosomes compared with the group treated with PBS, by 70.74±14.25% compared with the group treated with EXO-CON, and by 62.44±18.29% compared with the group treated with recombinant FAF1 (AngioLab, Korea). In addition, as shown in FIGS. 14*c* and 14*d*, it was confirmed that the tumor weight decreased by 73.48±33.22% in the group treated with FAF1-loaded exosomes compared with the group treated with PBS, by 66.62±42.16% compared with the group treated with EXO-CON, and by 44.44±70.87% compared with the group treated with recombinant FAF1 (AngioLab, Korea). In addition, as shown in FIG. 14*e*, it was confirmed that necrosis occurred inside the tumor of the group treated with EXO-FAF1.

<3-5> Evaluation of Efficacy in Triple Negative Breast Cancer Xenotransplanted Animal Models MDA-MB-231 cell lines, which are triple negative breast cancer cell lines, were xenotransplanted into immunodeficient nude mice to confirm whether FAF1-loaded exosomes have the ability to suppress the tumor formation.

As a result, as shown in FIGS. 15*a* and 15*b*, it was confirmed that the tumor volume decreased by 80.38±8.34% in the group treated with FAF1-loaded exosomes compared with the group treated with PBS, by 68.32±13.46% compared with the group treated with EXO-CON, and by 67.22±13.93% compared with the group treated with recombinant FAF1 (AngioLab, Korea). In addition, as shown in FIGS. 15*c* and 15*d*, it was confirmed that the tumor weight decreased by 77.03±11.83% in the group treated with FAF1-loaded exosomes compared with the group treated with PBS, by 69.63±15.66% compared with the group treated with EXO-CON, and by 62.50±19.33% compared with the group treated with recombinant FAF1 (AngioLab, Korea). In addition, as shown in FIG. 15*e*, it was confirmed that necrosis occurred inside the tumor of the group treated with EXO-FAF1.

<3-6> Evaluation of Efficacy in Kidney Cancer Xenotransplanted Animal Models

Caki-1 cell lines, which are kidney cancer cell lines, were xenotransplanted into immunodeficient nude mice to confirm whether FAF1-loaded exosomes have the ability to suppress the tumor formation.

As a result, as shown in FIGS. 16*a* and 16*b*, it was confirmed that the tumor volume decreased by 54.23±12.40% in the group treated with FAF1-loaded exosomes compared with the group treated with PBS, by 43.05±15.21% compared with the group treated with EXO-CON, and by 53.56±12.60% compared with the group treated with recombinant FAF1 (AngioLab, Korea). In addition, as shown in FIGS. 16*c* and 16*d*, it was confirmed that the tumor weight decreased by 42.11±16.22% in the group treated with FAF1-loaded exosomes compared with the group treated with PBS, by 31.25±19.26% compared with the group treated with recombinant FAF1 (AngioLab, Korea). In addition, as shown in FIG. 16*e*, it was confirmed that necrosis occurred inside the tumor of the group treated with EXO-FAF1.

<3-7> Evaluation of Efficacy in Cervical Cancer Xenotransplanted Animal Models

HeLa cells, which are cervical cancer cell lines, were xenotransplanted into immunodeficient nude mice to confirm whether FAF1-loaded exosomes have the ability to suppress the tumor formation.

As a result, as shown in FIGS. 17*a* and 17*b*, it was confirmed that the tumor volume decreased by 66±11.33% in the group treated with FAF1-loaded exosomes compared with the group treated with PBS, by 56.4±14.52% compared with the group treated with EXO-CON, and by 57.1±14.30% compared with the group treated with recombinant FAF1 (AngioLab, Korea). In addition, as shown in FIGS. 17*c* and 17*d*, it was confirmed that the tumor weight decreased by 60±17.59% in the group treated with FAF1-loaded exosomes compared with the group treated with PBS, by 48.6±21.39% compared with the group treated with EXO-CON, and by 70.7±12.17% compared with the group treated with recombinant FAF1 (AngioLab, Korea). In addition, as shown in FIG. 17*e*, it was confirmed that necrosis occurred inside the tumor of the group treated with EXO-FAF1.

The invention claimed is:

1. A method for treating cancer in a subject in need thereof, the method comprising administering to the subject an effective amount of the pharmaceutical composition comprising an isolated population of FAF1 protein-loaded exosomes.

2. The method of claim 1, wherein the FAF1 protein comprises the amino acid sequence of SEQ ID NO: 1.

3. The method of claim 1, wherein the exosomes have a diameter of 50-200 nm.

4. The method of claim 1, wherein the FAF1 protein loaded in the exosomes suppresses the tumor formation of other cells.

5. The method of claim 1, wherein the cancer is cervical cancer, pancreatic cancer, liver cancer, lung cancer, breast cancer, kidney cancer, colorectal cancer, squamous cell carcinoma of the head and neck, bladder cancer, prostate cancer, gastric cancer, endometrial cancer, brain cancer, ovarian cancer, testicular cancer, head cancer, neck cancer, skin cancer, mesothelial lining cancer, esophageal cancer, adrenal cancer, thyroid cancer, bone cancer, glioblastoma, mesothelioma, sarcoma, choriocarcinoma, cutaneous basal cell carcinoma, testicular seminoma, leukemia, or malignant lymphoma.

6. The method of claim 1, wherein the exosomes of the composition deliver FAF1 to target tumor cells.

7. The method of claim 1, wherein the composition is administered via oral administration, intrabronchial inhalation, or intraperitoneal, intrarectal, subcutaneous, intravenous, intramuscular, intrathoracic, or intratumoral injection.

8. The method of claim 1, further comprising administering to the subject an additional therapeutic agent.

* * * * *

SEQUENCE LISTING

```
<160> NUMBER OF SEQ ID NOS: 1

<210> SEQ ID NO 1
<211> LENGTH: 650
<212> TYPE: PRT
<213> ORGANISM: Artificial Sequence
```

<220> FEATURE:
<223> OTHER INFORMATION: FAS-associated factor 1 protein

<400> SEQUENCE: 1

Met Ala Ser Asn Met Asp Arg Glu Met Ile Leu Ala Asp Phe Gln Ala
1 5 10 15

Cys Thr Gly Ile Glu Asn Ile Asp Glu Ala Ile Thr Leu Leu Glu Gln
20 25 30

Asn Asn Trp Asp Leu Val Ala Ala Ile Asn Gly Val Ile Pro Gln Glu
35 40 45

Asn Gly Ile Leu Gln Ser Glu Tyr Gly Gly Glu Thr Ile Pro Gly Pro
50 55 60

Ala Phe Asn Pro Ala Ser His Pro Ala Ser Ala Pro Thr Ser Ser Ser
65 70 75 80

Ser Ser Ala Phe Arg Pro Val Met Pro Ser Arg Gln Ile Val Glu Arg
85 90 95

Gln Pro Arg Met Leu Asp Phe Arg Val Glu Tyr Arg Asp Arg Asn Val
100 105 110

Asp Val Val Leu Glu Asp Thr Cys Thr Val Gly Glu Ile Lys Gln Ile
115 120 125

Leu Glu Asn Glu Leu Gln Ile Pro Val Ser Lys Met Leu Leu Lys Gly
130 135 140

Trp Lys Thr Gly Asp Val Glu Asp Ser Thr Val Leu Lys Ser Leu His
145 150 155 160

Leu Pro Lys Asn Asn Ser Leu Tyr Val Leu Thr Pro Asp Leu Pro Pro
165 170 175

Pro Ser Ser Ser Ser His Ala Gly Ala Leu Gln Glu Ser Leu Asn Gln
180 185 190

Asn Phe Met Leu Ile Ile Thr His Arg Glu Val Gln Arg Glu Tyr Asn
195 200 205

Leu Asn Phe Ser Gly Ser Ser Thr Ile Gln Glu Val Lys Arg Asn Val
210 215 220

Tyr Asp Leu Thr Ser Ile Pro Val Arg His Gln Leu Trp Glu Gly Trp
225 230 235 240

Pro Thr Ser Ala Thr Asp Asp Ser Met Cys Leu Ala Glu Ser Gly Leu
245 250 255

Ser Tyr Pro Cys His Arg Leu Thr Val Gly Arg Arg Ser Ser Pro Ala
260 265 270

Gln Thr Arg Glu Gln Ser Glu Glu Gln Ile Thr Asp Val His Met Val
275 280 285

Ser Asp Ser Asp Gly Asp Asp Phe Glu Asp Ala Thr Glu Phe Gly Val
290 295 300

Asp Asp Gly Glu Val Phe Gly Met Ala Ser Ser Ala Leu Arg Lys Ser
305 310 315 320

Pro Met Met Pro Glu Asn Ala Glu Asn Glu Gly Asp Ala Leu Leu Gln
325 330 335

Phe Thr Ala Glu Phe Ser Ser Arg Tyr Gly Asp Cys His Pro Val Phe
340 345 350

Phe Ile Gly Ser Leu Glu Ala Ala Phe Gln Glu Ala Phe Tyr Val Lys
355 360 365

Ala Arg Asp Arg Lys Leu Leu Ala Ile Tyr Leu His His Asp Glu Ser
370 375 380

Val Leu Thr Asn Val Phe Cys Ser Gln Met Leu Cys Ala Glu Ser Ile
385 390 395 400

-continued

```
Val Ser Tyr Leu Ser Gln Asn Phe Ile Thr Trp Ala Trp Asp Leu Thr
                405                 410                 415

Lys Asp Ser Asn Arg Ala Arg Phe Leu Thr Met Cys Asn Arg His Phe
            420                 425                 430

Gly Ser Val Val Ala Gln Thr Ile Arg Thr Gln Lys Thr Asp Gln Phe
        435                 440                 445

Pro Leu Phe Leu Ile Ile Met Gly Lys Arg Ser Ser Asn Glu Val Leu
    450                 455                 460

Asn Val Ile Gln Gly Asn Thr Thr Val Asp Glu Leu Met Met Arg Leu
465                 470                 475                 480

Met Ala Ala Met Glu Ile Phe Thr Ala Gln Gln Gln Glu Asp Ile Lys
                485                 490                 495

Asp Glu Asp Glu Arg Glu Ala Arg Glu Asn Val Lys Arg Glu Gln Asp
            500                 505                 510

Glu Ala Tyr Arg Leu Ser Leu Glu Ala Asp Arg Ala Lys Arg Glu Ala
        515                 520                 525

His Glu Arg Glu Met Ala Glu Gln Phe Arg Leu Glu Gln Ile Arg Lys
    530                 535                 540

Glu Gln Glu Glu Glu Arg Glu Ala Ile Arg Leu Ser Leu Glu Gln Ala
545                 550                 555                 560

Leu Pro Pro Glu Pro Lys Glu Glu Asn Ala Glu Pro Val Ser Lys Leu
                565                 570                 575

Arg Ile Arg Thr Pro Ser Gly Glu Phe Leu Glu Arg Arg Phe Leu Ala
            580                 585                 590

Ser Asn Lys Leu Gln Ile Val Phe Asp Phe Val Ala Ser Lys Gly Phe
        595                 600                 605

Pro Trp Asp Glu Tyr Lys Leu Leu Ser Thr Phe Pro Arg Arg Asp Val
    610                 615                 620

Thr Gln Leu Asp Pro Asn Lys Ser Leu Leu Glu Val Lys Leu Phe Pro
625                 630                 635                 640

Gln Glu Thr Leu Phe Leu Glu Ala Lys Glu
                645                 650
```